US010870854B2

(12) United States Patent
Zhu et al.

(10) Patent No.: US 10,870,854 B2
(45) Date of Patent: Dec. 22, 2020

(54) INHIBITORY RNA-BASED THERAPEUTICS TARGETING ANLN FOR CANCER TREATMENT

(71) Applicant: The Board of Regents of the University of Texas System, Austin, TX (US)

(72) Inventors: Hao Zhu, Dallas, TX (US); Shuyuan Zhang, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 16/308,669

(22) PCT Filed: May 24, 2017

(86) PCT No.: PCT/US2017/034142
§ 371 (c)(1),
(2) Date: Dec. 10, 2018

(87) PCT Pub. No.: WO2017/213851
PCT Pub. Date: Dec. 14, 2017

(65) Prior Publication Data
US 2019/0153448 A1 May 23, 2019

Related U.S. Application Data

(60) Provisional application No. 62/347,803, filed on Jun. 9, 2016.

(51) Int. Cl.
| | |
|---|---|
| C12N 15/11 | (2006.01) |
| C12N 15/113 | (2010.01) |
| A61P 35/00 | (2006.01) |
| A61K 9/127 | (2006.01) |
| A61K 9/51 | (2006.01) |
| A61K 31/7088 | (2006.01) |
| A61K 45/06 | (2006.01) |
| A61N 5/10 | (2006.01) |

(52) U.S. Cl.
CPC ............ *C12N 15/113* (2013.01); *A61K 9/127* (2013.01); *A61K 9/51* (2013.01); *A61K 31/7088* (2013.01); *A61K 45/06* (2013.01); *A61N 5/1077* (2013.01); *A61P 35/00* (2018.01); *C12N 2310/14* (2013.01); *C12N 2310/351* (2013.01); *C12N 2310/531* (2013.01); *C12N 2320/31* (2013.01); *C12N 2330/51* (2013.01)

(58) Field of Classification Search
None
See application file for complete search history.

(56) References Cited

U.S. PATENT DOCUMENTS

| | | | |
|---|---|---|---|
| 2009/0297500 A1 | 12/2009 | Nakamura et al. | |
| 2010/0184830 A1* | 7/2010 | Croce | C12N 15/1135 514/44 R |
| 2011/0054005 A1 | 3/2011 | Naito et al. | |
| 2014/0106352 A1 | 4/2014 | Gbadesgesin et al. | |

OTHER PUBLICATIONS

Wang et al, F-actin binding protein, anillin, regulates integrity of intercellular junctions in human epithelial cells, Cell. Mol. Life Sci., 2015, 72: 3185-3200 (Year: 2015).*
D'Avino et al., "Isolation of protein complexes involved in mitosis and cytokinesis from *Drosophila* cultured cells," *Methods Mol Biol*, 545:99-112, 2009.
Field and Alberts, "Anillin, a contractile ring protein that cycles from the nucleus to the cell cortex," *J Cell Biol*, 131(1):165-178, 1995.
Giansanti et al., "The role of anillin in meiotic cytokinesis of *Drosophila* males," *J Cell Science*, 112(14):2323-2334, 1999.
Hall et al., "The septin-binding protein anillin is overexpressed in diverse human tumors," *Clin Cancer Res*, 11(19 Pt 1):6780-6786, 2005.
Hickson and O'Farrell, "Anillin: a pivotal organizer of the cytokinetic machinery," *Biochem Soc Trans*, 36(Pt 3):439-441, 2008.
Oegema et al., "Functional analysis of a human homologue of the *Drosophila* actin binding protein anillin suggests a role in cytokinesis," *J Cell Biology*, 150(3):539-552, 2000.
PCT International Preliminary Report on Patentability issued in International Application No. PCT/US2017/034142, dated Dec. 20, 2018.
PCT International Search Report and Written Opinion issued in International Application No. PCT/US2017/034142, dated Aug. 16, 2017.
Piekny and Maddox, "The myriad roles of Anillin during cytokinesis," *Semin Cell Dev Biol*, 21(9):881-891, 2010.
Straight et al., "Anillin binds nonmuscle myosin II and regulates the contractile ring," *Molecular Biology of the Cell*, 16:193-201, 2005.
Suzuki et al., "ANLN plays a critical role in human lung carcinogenesis through the activation of RHOA and by involvement in the phosphoinositide 3-kinase/AKT pathway," *Cancer Res.*, 65(24):11314-11325, 2005.
Wang et al., "Overexpression of Anillin (ANLN) is correlated with colorectal cancer progression and poor prognosis," *Cancer Biomark*, 16(3):459-465, 2016.
Zhang et al., "Defining the role of polyploidy in mouse liver," Speaker Abstract, ISSCR Annual Meeting, San Francisco, 2016.

(Continued)

*Primary Examiner* — Ekaterina Poliakova-Georgantas
(74) *Attorney, Agent, or Firm* — Parker Highlander PLLC

(57) ABSTRACT

Embodiments of the present disclosure include compositions and methods related to certain siRNA compositions for the treatment of cancer. In specific embodiments, siRNAs are employed for treatment of cancer, including at least liver cancer. Therapeutic methods, compositions, and kits are encompassed in the disclosure.

14 Claims, 18 Drawing Sheets

Specification includes a Sequence Listing.

(56) References Cited

OTHER PUBLICATIONS

Zhao and Fang, "Anillin is a substrate of anaphase-promoting complex/cyclosome (APC/C) that controls spatial contractility of myosin during late cytokinesis," *The Journal of Biological Chemistry*, 280(39):33516-33524, 2005.

Zhou et al., "Knockdown of ANLN by lentivirus inhibits cell growth and migration in human breast cancer," *Mol Cell Biochem*, 398(1-2):11-19, 2015.

* cited by examiner

INHIBITORY RNA-BASED THERAPEUTICS TARGETING ANLN FOR CANCER TREATMENT

PRIORITY CLAIM

This application is a national phase application under 35 U.S.C. § 371 of International Application No. PCT/US2017/034142, filed May 24, 2017, which claims benefit of priority to U.S. Provisional Application Ser. No. 62/347,803 filed Jun. 9, 2016, the entire contents of each of which are hereby incorporated by reference.

This invention was made with government support under grant no. K08 CA157727, awarded by the National Cancer Institute/National Institutes of Health. The government has certain rights in the invention.

BACKGROUND

1. Field of the Invention

Embodiments of the present invention concern at least the fields of molecular biology, cell biology, medicine and oncology. In specific embodiments, the field includes treatment and/or prevention of cancer with siRNA composition(s) directed to anillin actin-binding protein (Anln).

2. Description of Related Art

Cytokinesis is the last step of mitosis, and is essential for complete cell division (Barr and Gruneber, 2007). This process is shared by all mitotic cells. In most organs, targeting cytokinesis to fight cancer could lead to detrimental outcomes for normal cells undergoing division (Fujiwara et al., 2005; Pampalona et al., 2012; Lv et al., 2012; Hognas et al., 2012). In addition, it is possible that cytokinesis failure could increase the risk of chromosomal mis-segregation (Fujiwara et al., 2005; Lv et al., 2012; Hognas et al., 2012; Niu et al., 2017; Mittal et al., 2017; Davoli et al., 2017). However, uniquely, the liver naturally harbors a significant number of aneuploid and polyploid cells (Duncan et al., 2013; 2012a; 2010). During development, rodent hepatocytes experience cytokinesis failure, resulting in a large percentage of adult hepatocytes that are polyploid, harboring 4, 8 or more copies of chromosomes in their nuclei, as oppose to normal 2c diploid cells (Gentric et al., 2012; Celton-Morizur et al., 2009; Margall-Ducos et al., 2007). It is most likely that developing human liver cells undergo the same process since human livers were also found to have large percentage of polyploid cells (Duncan et al., 2013; Simson, 1963; Duncan et al., 2012b). Therefore, the liver might give one a unique opportunity to investigate the possibility of inhibiting cytokinesis in the context of hepatocellular carcinoma.

SUMMARY

Thus, in accordance with the present disclosure, there is provided an interfering RNA that targets an anillin actin binding protein mRNA. The interfering RNA may be about 21-23 bases in length. The interfering RNA may exhibit at least 80%, 85%, 90% or 95% identical to SEQ ID NO: 1. The may comprise the sequence of SEQ ID NO: 1. The interfering RNA may consist of the sequence of SEQ ID NO: 1.

Another embodiment provides a recombinant polynucleotide vector comprising a sequence encoding an interfering RNA as defined above, operably linked to expression control sequence for expression of a polynucleotide. The expression control sequence may comprise a Pol I or Pol III promoter.

Also provided is a pharmaceutical composition comprising an interfering RNA as defined above in a pharmaceutically acceptable carrier. Also provided is pharmaceutical composition comprising a recombinant polynucleotide vector as defined above in a pharmaceutically acceptable carrier. The pharmaceutical composition may be associated with a liposome, a polymeric delivery vehicle or a nanoparticle.

In still another embodiment, there is provided a method of treating cancer in a subject comprising administering to the subject an effective amount of an interfering RNA, a vector, or a composition as defined above. Interfering RNA, vector or composition is delivered by liposome or nanoparticle. The cancer may be liver cancer. The interfering RNA, vector or composition may be administered systemically, regional to said cancer or local to said cancer. The interfering RNA, vector or composition may be administered intravenously, intratumorally, intrahepatically, intra-arterially, subcutaneously, topically or orally. The method may further comprise administering an additional anti-cancer therapy to the individual, such as surgery, radiation, chemotherapy, hormone therapy, immunotherapy, or a combination thereof. The radiation may comprise external beam radiation therapy. The administering step may be repeated. The cancer may be recurrent, metastatic or drug resistant.

In one embodiment, the siRNA compositions are administered prior to administration of an anti-cancer therapy, including chemotherapy, radiotherapy, hormone therapy, immunotherapy, and so forth, to sensitize cells to the effects of the anti-cancer therapy. The compositions are administered to an individual in need of treatment of at least one symptom or manifestation (since disease can occur/progress in the absence of symptoms) of cancer. The compositions can be administered alone or in combination with adjuvant cancer therapy, such as surgery, chemotherapy, radiotherapy, thermotherapy, immunotherapy, hormone therapy, and/or laser therapy, to provide a beneficial effect, e.g., reduce tumor size, reduce cell proliferation of the tumor, inhibit angiogenesis, inhibit metastasis, or otherwise improve at least one symptom or manifestation of the disease.

Also provided is kit for treating cancer in an individual, said kit comprising an interfering RNA, a recombinant polynucleotide vector, or a pharmaceutical composition, disposed in suitable container.

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the invention may "consist essentially of" or "consist of" one or more sequences of the invention, for example. Some embodiments of the invention may consist of or consist essentially of one or more elements, method steps, and/or methods of the invention. It is contemplated that any method or composition described herein can be implemented with respect to any other method or composition described herein. Embodiments discussed in the context of methods and/or compositions of the invention may be employed with respect to any other method or composition described herein. Thus, an embodiment pertaining to one method or composition may be applied to other methods and compositions of the invention as well.

Throughout this application, the term "about" is used to indicate that a value includes the standard deviation of error for the device or method being employed to determine the value.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Oncomine data showing human ANLN mRNA expression levels in normal liver and HCC tissues. (B) RT-qPCR data showing human ANLN mRNA expression levels in matched normal and HCC pairs.

(FIG. 2A) Schematic of retrovirus TRMPVIR construct. (FIG. 2B) Anln mRNA level in H2.35 cells was determined by RT-qPCR to assess knockdown efficiency of 10 different shAnlns compared to Sham and shScr. (FIG. 2C) Ploidy distribution in H2.35 cells treated with either shScr, shAnln #2, or shAnln #3. (FIG. 2D) Proliferation assays in uninduced and Dox-induced H2.35 cells containing either shScr, shAnln #2, or shAnln #3. (FIG. 2E) Live imaging of dividing H2.35 cells containing either shScr or shAnln #2 in the presence of Dox. (FIG. 2F) Immuno-fluorescence staining of the above cells with DAPI and β-catenin.

(FIG. 3A) A schematic showing how the FRG$^{-/-}$ transplantation experiment was conducted. (FIG. 3B) Gross liver imageS of FRG$^{-/-}$ mice transplanted with either shScr or shAnln with or without Dox induction. (FIG. 3C) Fluorescent images showing GFP positive clonal expansion of H2.35 donor cells containing either induced shScr or shAnln. (FIG. 3D) Quantification of GFP-positive H2.35 cells in panel C for shScr and shAnln groups.

(FIG. 4A) A schematic of LAP-tTA; TRE-MYC mouse model. (FIG. 4B) A schematic of induction and treatment regimen; Dox was withdrawn at p0 to induce human c-MYC expression. Treatment with in vivo siRNA packaged in lipid nanoparticles started at p10 twice/week at 2.0 mg/kg until p25 (two intraperitoneal and three retro-orbital). (FIG. 4C) Anln mRNA level was determined by RT-qPCR in H2.35 cells to test the knockdown efficiency of 3 different siAnln versus siScr. shAnln #1 was selected for subsequent animal experiments. (FIG. 4D) Ploidy distribution in H2.35 cells treated with either siScr or 3 different siAnln. (FIG. 4E) Anln mRNA level determined by RT-qPCR in MYC-indcued mouse liver treated with either in vivo siScr or siAnln. (FIG. 4F) Liver to body weight ratio of MYC-induced mice treated with either in vivo siScr or siAnln. (FIG. 4G) Gross liver images of MYC-induced mice treated with either in vivo siScr or siAnln. (FIG. 4H) H&E staining of the livers of the above mice. (FIG. 4I) Quantification of tumor area/field in the H&E staining in both siScr and siAnln treated mice. (FIG. 4J) Kaplan-Meier survival of of MYC-induced mice treated with either in vivo siScr or siAnln.

(FIG. 5A) An inducible double-transgenic mouse model carrying shAnln cassette under the control of a tetracycline responsive promoter element (TRE). These mice carry a Rosa-rtTA knockin construct, allowing induction of Anln suppression with Doxycycline (Dox) water. (FIG. 5B) Inducible TG-shAnln embryonic stem cells showing Anln expression levels after dox induction for 72 hours. (FIG. 5C) Western blot of Anln protein levels in embryonic stem cell clones after dox induction. (FIG. 5D) Rosa or TG-shAnln transgenic mice exposed to dox water from P0-P20 develop normally. (FIG. 5E) Body weight of the Rosa and TG-shAnln mice after dox water treatment from P0-P20. (FIG. 5F) AST/ALT serum liver function tests in these mice after dox treatment. (FIG. 5G) Transient Dox induction from P0 to P20 suppressed Anln mRNA levels in the liver. (FIG. 5H) Representative cellular ploidy distribution of TG-shAnln livers treated with dox from P0-P20 was determined by PI staining and flow cytometry at the age of P20 (left panel). On the right is the average ploidy distribution (n=3 mice in each group).

(FIG. 6A) Schema for the DEN plus CCL4 induced HCC experiment in inducible shRNA mice: at p15, mice were injected with DEN (25 µg/g). At p32 dox treatment was started and one week later (p39) CCL4 injury was started (IP injection, two times a week). Tumor burden was examined after 12 weeks of CCL4 injury. (FIG. 6B) Representative gross tumor burden from Rosa and TG-shAnln mice in the DEN plus CCL4 experiment. (FIG. 6C) Liver surface tumor quantification and liver to body weight ratio of the above mice.

(FIG. 7A) Anln mRNA level was determined by RT-qPCR in WT mice livers to test the knockdown efficiency of 6 different siAnln versus siLuc. Mice were injected with siRNAs subcutaneously at 1 mg/kg from p7 to p21, one time a week for two weeks. Livers were harvested at p21. siAnln #1 was selected for subsequent animal experiments (FIG. 7B) Ploidy distribution of above livers. (FIG. 7C) Liver function tests of the mice treated with two doses of siAnln or siLuc at 1 mg/kg, 4 days apart. Blood serum was taken at 3 days after the last dose (n=7). (FIG. 7D) Liver to body weight ratios before (resected) and 40 hours (regenerated) after partial hepatectomy. siRNA treated mice (two doses at 1 mg/kg, two doses with 4 days apart) underwent 70% partial hepatectomy at six weeks of age and remnant livers were harvested and analyzed 40 hours after surgery (n=7). (FIG. 7E) qPCR for liver differentiation genes in siRNA treated livers as described above (n=7).

DESCRIPTION OF ILLUSTRATIVE EMBODIMENTS

I. The Present Disclosure

Figure 1A:
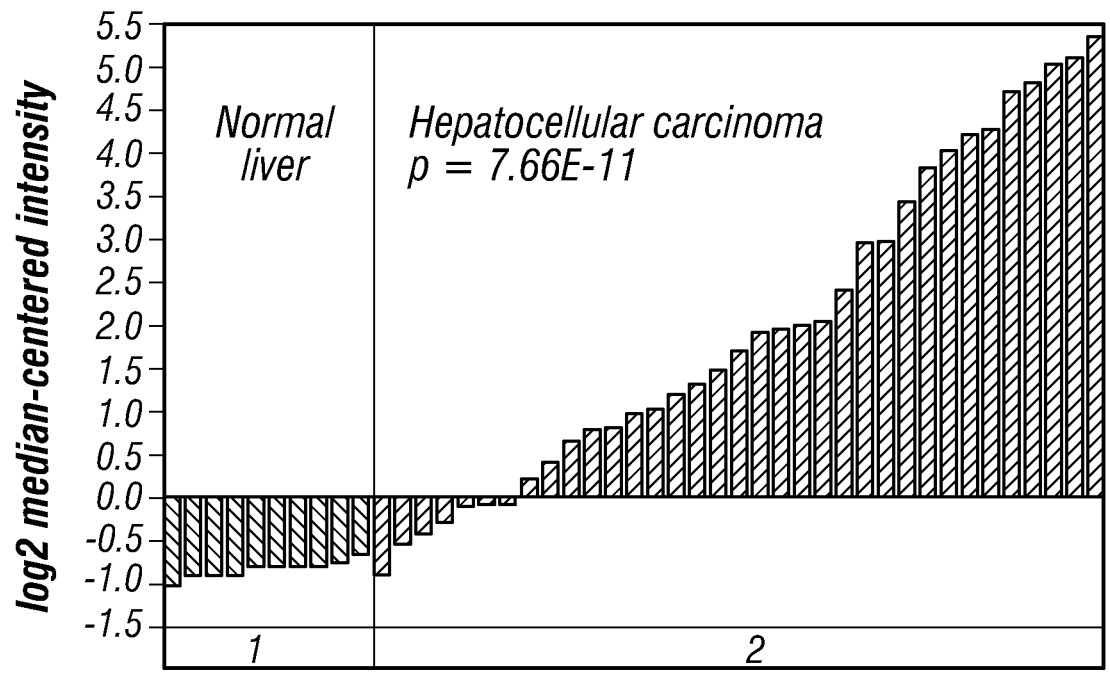
FIGS. 1A-B: Overexpression of human ANLN enhanced cancer cell growth both in vitro and in xenografts.
Figure 1A:
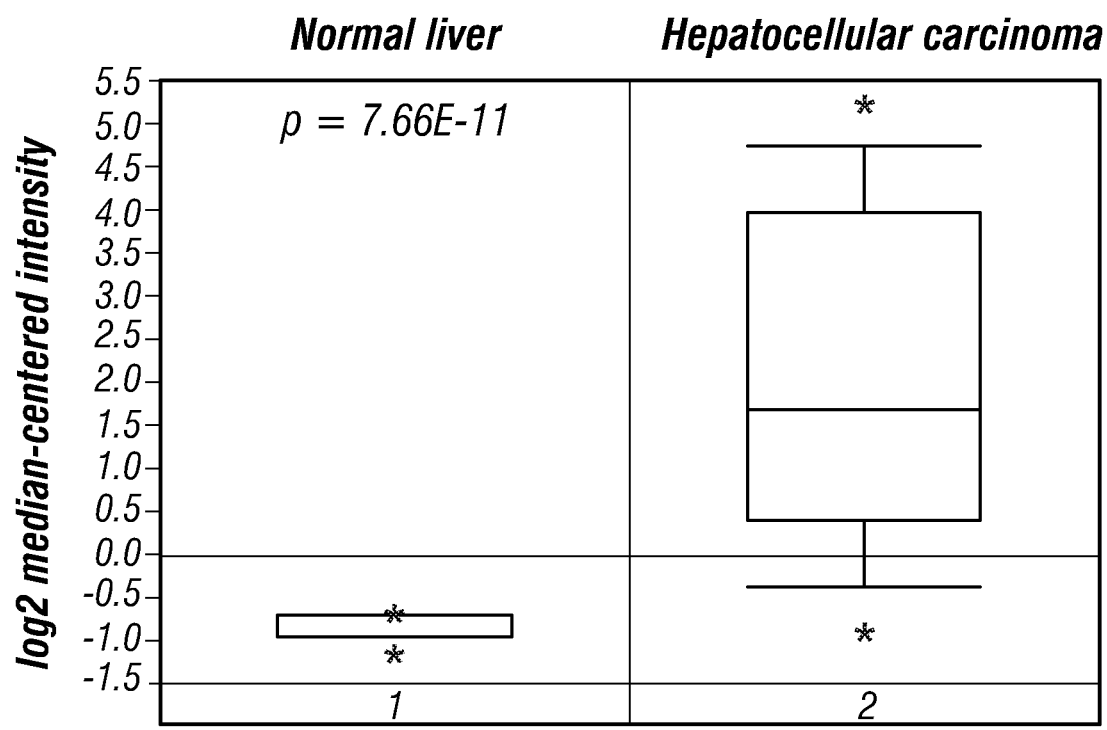

In cytokinesis, Anln is an essential molecule, and would serve as a good target if it were manipulatable given that its expression is upregulated in many cancer types. To this end, this present study took the approach of suppressing Anillin (Anln) expression to induce cytokinesis failure and examine its effect on liver regeneration and cancer development. Anln is a highly conserved actin binding protein that serves as a key mediator of cytokinesis (Hickson and O'Farrell, 2008; Piekny and Maddox, 2010). Anln can bind to all three types of actin filaments [(Piekny et al., 2010; D'Avino et al., 2009; Oegema et al., 2000), as well as RhoA, ECT2, myosin II, septins and other important cytoskeletal regulators, serving as a scaffolding protein to coordinate cytokinesis in time and space. Although the exact mechanism of how Anln functions in cytokinesis remains elusive, its presence is required during multiple steps of cytokinesis (Field and Alberts, 1995; Giansanti et al., 1999; Oegema et al., 2000).

Anln has also been linked to cancer given its role in cytokinesis. Human cancer mRNA profiling showed that ANLN expression is upregulated in tumor tissues by 2-6 folds compared to the surrounding normal tissues (Piekney et al., 2010). Moreover, higher ANLN expression is correlated with higher metastatic frequency (Hall et al., 2005) and poor prognosis (Wang et al., 2016). It has also been shown that knocking down ANLN in breast cancer cell lines can inhibit cell proliferation (Zhou et al., 2015). These studies suggest that ANLN overexpression contributes to tumor growth and implicate ANLN as a potential therapeutic target. However, there is no evidence about the role of ANLN in hepatocellular carcinoma (HCC) or the effect of its suppression on cytokinesis and ploidy in both the tumor and normal liver.

In liver cancer cell lines, the inventors found that suppressing Anln using shRNA effectively induces cytokinesis failure, which led to decreased cell growth in vitro and impaired tumor forming ability in a liver transplantation assay. To study this phenomenon in animal models, they made use of an aggressive MYC-induced liver cancer model and found that inhibiting Anln via in vivo siRNA could significantly delay the tumorigenesis and extend survival of these mice. Furthermore, the inventors engineered an inducible shAnln transgenic mouse model and found these mice had suppressed tumorigenesis in DEN plus CCL4 liver cancer model. While inhibiting Anln suppression effectively inhibits liver tumorigenesis, it did not cause any noticeable damages to the liver tissues, nor affecting liver functions and its capacity to regenerate. Collectively, these results demonstrated that inducing cytokinesis failure via suppression of Anln could inhibit liver cancer development without affecting tissue homeostasis and regenerative capacity of the liver.

These and other aspects of the disclosure are discussed further below.

II. Anillin Acting Binding Protein

Anillin is a conserved protein implicated in cytoskeletal dynamics during cellularization and cytokinesis. The ANLN gene in humans and the scraps gene in *Drosophila* encode Anillin. In 1989, anillin was first isolated in embryos of *Drosophila melanogaster*. It was identified as an F-actin binding protein. Six years later, the anillin gene was cloned from cDNA originating from a *Drosophila* ovary. Staining with anti-anillin (Antigen 8) antibody showed the anillin localizes to the nucleus during interphase and to the contractile ring during cytokinesis. These observations agree with further research that found anillin in high concentrations near the cleavage furrow coinciding with RhoA, a key regulator of contractile ring formation.

The name of the protein anillin originates from a Spanish word, anillo. Anillo means ring and shows that the name anillin references the observed enrichment of anillins at the contractile ring during cytokinesis. Anillins are also enriched at other actomyosin rings, most significantly, those at the leading edge of the *Drosophila* embryo during cellularization. These actomyosin rings invaginate to separate all nuclei for one another in the syncytial blastoderm.

A. Structure

Anillin has a unique multi-domain structure. At the N-terminus, there is an actin- and myosin-binding domain. At the C-terminus, there is a PH domain. The PH domain is conserved and essential for anillin functionality. The human anillin cDNA, located on Chr7, encodes a 1,125-amino acid protein with a predicted molecular mass of 124 kD and a pI of 8.1. The mouse anillin gene is located on Chr9. There are also numerous anillin-like protein homologues found outside of metazoans. In *Schizosaccharomyces pombe* (fission yeast), there are Mid1p and Mid2p. These two anillin-like proteins do not have any overlap in their functions. Mid1p has been characterized as a key regulator in cytokinesis, responsible for arranging contractile ring assembly and positioning. Mid2p acts later in cytokinesis to organize septins during septation, or the invagination of inner membranes, outer membranes, and the cell wall that occurs in order to separate daughter cells completely. *Saccharomyces cerevisiae* (budding yeast) also have two anillin-like proteins, Boi1p and Boi2p. Boi1p and Boi2p localize to the nucleus and contractile ring at the bud neck, respectively. They are essential for cell growth and bud formation.

B. Anln Function

Anillins are required for the faithfulness of cytokinesis and its F-actin-, myosin-, and septin-binding domains implicate anillin in actomyosin cytoskeletal organization. In agreement with this belief, anillin-mutant cells have disrupted contractile rings. Additionally, it is hypothesized that anillin couples the actomyosin cytoskeleton to microtubules by binding MgcRacGAP/CYK-4/RacGAP50C. Anillins have also been shown to organize the actomyosin cytoskeleton into syncytial structures observed in *Drosophila* embryos or *C. elegans* gonads. ANI-1 and ANI-2 (proteins homologous to anillin) are essential for embryonic viability in both organisms. ANI-1 is required for cortical ruffling, pseudocleavage, and all contractile events that occur in embryos prior to mitosis. ANI-1 is also crucial for segregation of polar bodies during meiosis. Interestingly, ANI-2 functions in the maintenance of the structure of the central core of the cytoplasm, the rachis, during oogenesis. ANI-2 ensures oocytes do not disconnect prematurely from the rachis, thereby leading to the generation of embryos of varying sizes.

Anillins in metazoans are heavily phosphorylated; however, the kinases responsible for the phosphorylation are unknown at the present time. In humans and *Drosophila*, anillins are recruited to the equatorial cortex in a RhoA-dependent manner. This recruitment is independent of other cytoskeletal Rho targets such as myosin, F-actin, and Rho-kinase. It has been observed that anillin proteolysis is triggered after mitotic exit by the Anaphase Promoting Complex (APC). Most anillins can be sequestered to the nucleus during interphase, but there are exceptions—*Drosophila* anilins in the early embryo, *C. elegans* ANI-1 in early embryos, *C. elegans* ANI-2 in oogenic gonads, and Mid2p in fission yeast. These anillins that are not sequestered during interphase suggest that anillins may also regulate cytoskeletal dynamics outside the contractile ring during cytokinesis.

Anillin is critical for cell division and therefore development and homeostasis in metazoans. In recent years, the expression levels of anillin have been shown to correlate to the metastatic potential of human tumors. In colorectal cancer, expression levels of anillin are higher in tumors and when anillin was over-expressed in HT29 cells, a classical colorectal cancer cell line, the cells showed faster replication kinetics due to the lengthening of G2/M phase. Increasing the expression of anillin also led to further invasiveness and migration of numerous colorectal cancer cell lines. The hypothesis from such observations is that anillin promotes EMT and cell migration through cytoskeletal remodeling, leading to enhanced proliferation, invasion, and mobility of tumor cells.

C. Anln Binding Partners

The following is a discussion of Anln binding partners:

Actin. Anillin specifically binds F-actin, rather than G-actin. Binding of F-actin by anillin only occurs during cell division. Anillin is also bundles actin filaments together. Amino acids 258-340 are sufficient and necessary for F-actin binding in *Drosophila*, but amino acids 246-371 are necessary to bundle actin filaments. The ability of anillin to bind to and bundle actin together is conversed through many species. It is hypothesized that by regulating actin bundling, anillin increases the efficiency of actomyosin contractility during cell division. Both anillin and F-actin are found in contractile structures. They are recruited independently to the contractile ring, but F-actin increases the efficiency of anillin targeting. Anillin may also be involved in promoting the polymerization of F-actin by stabilizing formin mDia2 in an active form.

Myosin. Anillin interacts directly with non-muscle myosin II and interacts indirectly with myosin via F-actin. Residues 142-254 (near the N-terminus) are essential for anillin binding myosin in *Xenopus*. The interaction of anillin and myosin is also dependent on phosphorylation of the myosin light chain. The interaction of myosin and anillin does not seem to serve in recruitment, but rather organization of myosin. In *Drosophila*, anillin is necessary to organize myosin into rings in the cellularization front. Depletion of anillin in *Drosophila* and humans leads to changes in the spatial and temporal stability of myosin during cytokinesis. In *C. elegans*, ANI-1 organizes myosin into foci during cytokinesis and establishment of polarity, whereas, ANI-2 is a requirement for the maintenance of myosin-rich contractile lining of oogenic gonads.

Septins. Septin localization during cytokinesis and cellularization is dependent on its association with anillin. The direct interaction between anillin and septins was first shown by the interaction seen between *Xenopus* anillin and a minimal reconstituted heterooligomer of human septins 2, 6, and 7. The ability of anillin to bind to septins is dependent on the C-terminal domain, which contains a terminal PH domain and an upstream sequence known as the "Anillin Homology" (AH) domain.

Rho. The AH domain of human anillin is essential for its interaction with RhoA. Depletion of RhoA halts contractile ring assembly and ingression, whereas, anillin depletion leads to a less severe phenotype when the contractile ring forms and ingresses partially. Depletion of anillin in *Drosophila* spermatocytes greatly reduces the localization of Rho and F-actin to equatorial regions.

Ect2. Anillin interacts with Ect2, further supporting the idea that anillin stabilizes RhoA localization since Ect2 is an activator of RhoA. Independent of RhoA, the interaction between anillin and Ect2 occurs. This interaction is essential of the GEF activity of Ect2 and requires the AH domain of anillin and the PH domain of Ect2.

Cyk-4. *Drosophila* anillin interacts with Cyk-4, a central spindle protein, indicating that anillin may have a role in determining the division plane during cytokinesis. In anillin-depleted larval cells, the central spindle does not extend to the cortex. Human anillin-depleted cells show improperly positioned and distorted central spindles.

Microtubules. Anillin was first isolated from *Drosophila* by harnessing its interactions with both F-actin and microtubules. Furthermore, anillin-rich structures that form after Latrunculin A treatment of *Drosophila* cells localize to the plus-ends of microtubules. The interaction between anillin and microtubules suggest that anillin may serve as a signaling factor to relay the position of the mitotic spindle to the cortex to ensure appropriate contractile ring formation during cytokinesis.

III. siRNA Molecules

RNA interference (also referred to as "RNA-mediated interference" or RNAi) is a mechanism by which gene expression can be reduced or eliminated. Double-stranded RNA (dsRNA) has been observed to mediate the reduction, which is a multi-step process. dsRNA activates post-transcriptional gene expression surveillance mechanisms that appear to function to defend cells from virus infection and transposon activity (Fire et al., 1998; Grishok et al., 2000; Ketting et al., 1999; Lin and Avery et al., 1999; Montgomery et al., 1998; Sharp and Zamore, 2000; Tabara et al., 1999). Activation of these mechanisms targets mature, dsRNA-complementary mRNA for destruction. RNAi offers major experimental advantages for study of gene function. These advantages include a very high specificity, ease of movement across cell membranes, and prolonged down-regulation of the targeted gene (Fire et al., 1998; Grishok et al., 2000; Ketting et al., 1999; Lin and Avery et al., 1999; Montgomery et al., 1998; Sharp et al., 1999; Sharp and Zamore, 2000; Tabara et al., 1999). Moreover, dsRNA has been shown to silence genes in a wide range of systems, including plants, protozoans, fungi, *C. elegans, Trypanasoma, Drosophila*, and mammals (Grishok et al., 2000; Sharp et al., 1999; Sharp and Zamore, 2000; Elbashir et al., 2001). It is generally accepted that RNAi acts post-transcriptionally, targeting RNA transcripts for degradation. It appears that both nuclear and cytoplasmic RNA can be targeted (Bosher and Labouesse, 2000).

siRNAs must be designed so that they are specific and effective in suppressing the expression of the genes of interest. Methods of selecting the target sequences, i.e., those sequences present in the gene or genes of interest to which the siRNAs will guide the degradative machinery, are directed to avoiding sequences that may interfere with the siRNA's guide function while including sequences that are specific to the gene or genes. siRNA molecules ("siRNAs") are generally 19 to 23 nucleotides in length, and more specifically 21, 22 or 23 bases. Typically, siRNA target sequences of about 21-23 nucleotides in length are most effective. This length reflects the lengths of digestion products resulting from the processing of much longer RNAs as described above (Montgomery et al., 1998).

The present disclosure contemplates the design, synthesis and use of siRNA directed at Anln. In other words, these siRNAs will target Anln transcripts to reduce or "silence" Anln expression. siRNAs can be designed according to standard procedures in view of the Anln mRNA sequence, which can be found at NM_018685 (SEQ ID NO: 2), and the protein sequence for Anln can be found at NP_061155 (SEQ ID NO: 3). Specific siRNA compositions can comprise GGCUCUCUGCAGAUACUAATT (SEQ ID NO: 1).

The production of siRNAs has been mainly through direct chemical synthesis; through processing of longer, double-stranded RNAs through exposure to *Drosophila* embryo lysates; or through an in vitro system derived from S2 cells. Use of cell lysates or in vitro processing may further involve the subsequent isolation of the short, 21-23 nucleotide siRNAs from the lysate, etc., making the process somewhat cumbersome and expensive. Chemical synthesis proceeds by making two single-stranded RNA-oligomers followed by the annealing of the two single-stranded oligomers into a double-stranded RNA. Methods of chemical synthesis are diverse. Non-limiting examples are provided in U.S. Pat. Nos. 5,889,136, 4,415,723, and 4,458,066, expressly incorporated herein by reference, and in Wincott et al. (1995).

Several further modifications to siRNA sequences have been suggested in order to alter their stability or improve their effectiveness. It is suggested that synthetic complementary 21-mer RNAs having di-nucleotide overhangs (i.e., 19 complementary nucleotides+3' non-complementary dimers) may provide the greatest level of suppression. These protocols primarily use a sequence of two (2'-deoxy) thymidine nucleotides as the di-nucleotide overhangs. These dinucleotide overhangs are often written as dTdT to distinguish them from the typical nucleotides incorporated into RNA. The literature has indicated that the use of dT overhangs is primarily motivated by the need to reduce the cost of the chemically synthesized RNAs. It is also suggested that the dTdT overhangs might be more stable than UU overhangs, though the data available shows only a slight (<20%) improvement of the dTdT overhang compared to an siRNA with a UU overhang.

Chemically synthesized siRNAs are found to work optimally when they are in cell culture at concentrations of 25-100 nM, but concentrations of about 100 nM have achieved effective suppression of expression in mammalian cells. siRNAs have been most effective in mammalian cell culture at about 100 nM. In several instances, however, lower concentrations of chemically synthesized siRNA have been used (Caplen, et al., 2000; Elbashir et al., 2001).

WO 99/32619 and WO 01/68836 suggest that RNA for use in siRNA may be chemically or enzymatically synthesized. Both of these texts are incorporated herein in their entirety by reference. The enzymatic synthesis contemplated in these references is by a cellular RNA polymerase or a bacteriophage RNA polymerase (e.g., T3, T7, SP6) via the use and production of an expression construct as is known in the art. For example, see U.S. Pat. No. 5,795,715. The contemplated constructs provide templates that produce RNAs that contain nucleotide sequences identical to a portion of the target gene. The length of identical sequences provided by these references is at least 25 bases, and may be as many as 400 or more bases in length. An important aspect of this reference is that the authors contemplate digesting longer dsRNAs to 21-25-mer lengths with the endogenous nuclease complex that converts long dsRNAs to siRNAs in vivo. They do not describe or present data for synthesizing and using in vitro transcribed 21-25-mer dsRNAs. No distinction is made between the expected properties of chemical or enzymatically synthesized dsRNA in its use in RNA interference.

Similarly, WO 00/44914, incorporated herein by reference, suggests that single strands of RNA can be produced enzymatically or by partial/total organic synthesis. Preferably, single-stranded RNA is enzymatically synthesized from the PCR products of a DNA template, preferably a cloned cDNA template and the RNA product is a complete transcript of the cDNA, which may comprise hundreds of nucleotides. WO 01/36646, incorporated herein by reference, places no limitation upon the manner in which the siRNA is synthesized, providing that the RNA may be synthesized in vitro or in vivo, using manual and/or automated procedures. This reference also provides that in vitro synthesis may be chemical or enzymatic, for example using cloned RNA polymerase (e.g., T3, T7, SP6) for transcription of the endogenous DNA (or cDNA) template, or a mixture of both. Again, no distinction in the desirable properties for use in RNA interference is made between chemically or enzymatically synthesized siRNA.

U.S. Pat. No. 5,795,715 reports the simultaneous transcription of two complementary DNA sequence strands in a single reaction mixture, wherein the two transcripts are immediately hybridized. The templates used are preferably of between 40 and 100 base pairs, and which is equipped at each end with a promoter sequence. The templates are preferably attached to a solid surface. After transcription with RNA polymerase, the resulting dsRNA fragments may be used for detecting and/or assaying nucleic acid target sequences.

A. Nucleic Acids siRNAs can be synthesized or produced chemically or recombinantly. They may be isolated and/or purified. The term "recombinant" may be used and this generally refers to a molecule that has been manipulated in vitro or that is the replicated or expressed product of such a molecule.

The term "nucleic acid" is well known in the art. A "nucleic acid" as used herein will generally refer to a molecule (one or more strands) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T," or a cytosine "C") or RNA (e.g., an A, a G, an uracil "U," or a C). The term "nucleic acid" encompass the terms "oligonucleotide" and "polynucleotide," each as a subgenus of the term "nucleic acid."

As used herein, "hybridization," "hybridizes," or "capable of hybridizing" is understood to mean the forming of a double or triple stranded molecule or a molecule with partial double or triple stranded nature. The term "anneal" as used herein is synonymous with "hybridize." The term "hybridization," "hybridize(s)," or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.5 M NaCl at temperatures of about 42° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions," and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

B. Nucleobases

As used herein a "nucleobase" refers to a heterocyclic base, such as for example a naturally occurring nucleobase (i.e., an A, T, G, C, or U) found in at least one naturally occurring nucleic acid (i.e., DNA and RNA) and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those purines or pyrimidines substituted by one or more of an alkyl, caboxyalkyl, amino, hydroxyl, halogen (i.e., fluoro, chloro, bromo, or iodo), thiol or alkyl-thiol moeity. Preferred alkyl (e.g., alkyl, caboxyalkyl, etc.) moieties comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N5N-diemethyladenine, an azaadenines, a 8-bromoadenine, a 8-hydroxyadenine, a 6-hydroxyaminopurine, a 6-thiopurine, a 4-(6-aminohexyl/cytosine)5 and the like. Other examples are well known to those of skill in the art.

A nucleobase may be comprised in a nucleoside or nucleotide, using any chemical or natural synthesis method described herein or known to one of ordinary skill in the art. Such nucleobase may be labeled or it may be part of a molecule that is labeled and contains the nucleobase.

C. Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T, or U) typically covalently attaches a 1 position of a pyrimidine to a 1'-position of a 5-carbon sugar (Kornberg and Baker, 1992).

D. Nucleotides

As used herein, a "nucleotide" refers to a nucleoside further comprising a "backbone moiety." A backbone moiety generally covalently attaches a nucleotide to another molecule comprising a nucleotide, or to another nucleotide to form a nucleic acid. The "backbone moiety" in naturally occurring nucleotides typically comprises a phosphorous moiety, which is covalently attached to a 5-carbon sugar. The attachment of the backbone moiety typically occurs at either the 3'- or 5'-position of the 5-carbon sugar However, other types of attachments are known in the art, particularly when a nucleotide comprises derivatives or analogs of a naturally occurring 5-carbon sugar or phosphorus moiety.

E. Nucleic Acid Analogs

A nucleic acid may comprise, or be composed entirely of, a derivative or analog of a nucleobase, a nucleobase linker moiety and/or backbone moiety that may be present in a naturally occurring nucleic acid. RNA with nucleic acid analogs may also be labeled according to methods of the disclosure. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see, for example, Scheit, 1980, incorporated herein by reference).

Additional non-limiting examples of nucleosides, nucleotides or nucleic acids comprising 5-carbon sugar and/or backbone moiety derivatives or analogs, include those in U.S. Pat. No. 5,681,947, which describes oligonucleotides comprising purine derivatives that form triple helixes with and/or prevent expression of dsDNA; U.S. Pat. Nos. 5,652,099 and 5,763,167, which describe nucleic acids incorporating fluorescent analogs of nucleosides found in DNA or RNA, particularly for use as fluorescent nucleic acids probes; U.S. Pat. No. 5,614,617, which describes oligonucleotide analogs with substitutions on pyrimidine rings that possess enhanced nuclease stability, U.S. Pat. Nos. 5,670,663, 5,872,232 and 5,859,221, which describe oligonucleotide analogs with modified 5-carbon sugars (i.e., modified 2'-deoxyfuranosyl moieties) used in nucleic acid detection; U.S. Pat. No. 5,446,137, which describes oligonucleotides comprising at least one 5-carbon sugar moiety substituted at the 4' position with a substituent other than hydrogen that can be used in hybridization assays; U.S. Pat. No. 5,886,165, which describes oligonucleotides with both deoxyribonucleotides with 3'-5' internucleotide linkages and ribonucleotides with 2'-5' internucleotide linkages; U.S. Pat. No. 5,714,606, which describes a modified internucleotide linkage wherein a 3'-position oxygen of the internucleotide linkage is replaced by a carbon to enhance the nuclease resistance of nucleic acids; U.S. Pat. No. 5,672,697, which describes oligonucleotides containing one or more 5'-methylene phosphonate internucleotide linkages that enhance nuclease resistance; U.S. Pat. Nos. 5,466,786 and 5,792,847, which describe the linkage of a substituent moiety which may comprise a drug or label to the 2' carbon of an oligonucleotide to provide enhanced nuclease stability and ability to deliver drugs or detection moieties; U.S. Pat. No. 5,223,618, which describes oligonucleotide analogs with a 2 or 3 carbon backbone linkage attaching the 4' position and 3' position of adjacent 5-carbon sugar moiety to enhanced cellular uptake, resistance to nucleases and hybridization to target RNA; U.S. Pat. No. 5,470,967, which describes oligonucleotides comprising at least one sulfamate or sulfamide internucleotide linkage that are useful as nucleic acid hybridization probes; U.S. Pat. Nos. 5,378,825, 5,777,092, 5,623,070, 5,610,289 and 5,602,240, which describe oligonucleotides with a three or four atom linker moiety replacing a phosphodiester backbone moiety used for improved nuclease resistance, cellular uptake and regulating RNA expression; U.S. Pat. No. 5,858,988, which describes hydrophobic carrier agent attached to the 2'-O position of oligonucleotides to enhanced their membrane permeability and stability; U.S. Pat. No. 5,214,136, which describes oligonucleotides conjugated to anthraquinone at the 5' terminus that possess enhanced hybridization to DNA or RNA, enhanced stability to nucleases; U.S. Pat. No. 5,700,922, which describes PNA-DNA-PNA chimeras wherein the DNA comprises 2'-deoxy-erythro-pentofuranosyl nucleotides for enhanced nuclease resistance, binding affinity, and ability to activate RNase H; and U.S. Pat. No. 5,708,154, which describes RNA linked to a DNA to form a DNA-RNA hybrid; U.S. Pat. No. 5,728,525, which describes the labeling of nucleoside analogs with a universal fluorescent label.

Additional teachings for nucleoside analogs and nucleic acid analogs are U.S. Pat. No. 5,728,525, which describes nucleoside analogs that are end-labeled, and U.S. Pat. Nos. 5,637,683, 6,251,666 (L-nucleotide substitutions), and U.S. Pat. No. 5,480,980 (7-deaza-2'deoxyguanosine nucleotides and nucleic acid analogs thereof).

F. Modified Nucleotides

Labeling methods and kits of the disclosure specifically contemplate the use of nucleotides that are both modified for attachment of a label and can be incorporated into an siRNA molecule. Such nucleotides include those that can be labeled with a dye, including a fluorescent dye, or with a molecule such as biotin. Labeled nucleotides are readily available; they can be acquired commercially or they can be synthesized by reactions known to those of skill in the art.

Modified nucleotides for use in the disclosure are not naturally occurring nucleotides, but instead, refer to prepared nucleotides that have a reactive moiety on them. Specific reactive functionalities of interest include: amino, sulfhydryl, sulfoxyl, ammosulfhydryl, azido, epoxide, isothiocyanate, isocyanate, anhydride, monochlorotriazme, dichlorotriazme, mono- or dihalogen substituted pyridine, mono- or disubstituted diazme, maleimide, epoxide, aziridme, sulfonyl halide, acid hande, alkyl hande, aryl hande, alkylsulfonate, N-hydroxysuccimmide ester, imido ester, hydrazine, azidomtrophenyl, azide, 3-(2-pyridyl dithio)-propionarmde, glyoxal, aldehyde, iodoacetyl, cyanomethyl ester, p-nitrophenyl ester, o-nitrophenyl ester, hydroxypyridine ester, carbonyl imidazole, and the other such chemical groups. In some embodiments, the reactive functionality may be bonded directly to a nucleotide, or it may be bonded to the nucleotide through a linking group. The functional moiety and any linker cannot substantially impair the ability of the nucleotide to be added to the siRNA or to be labeled. Representative linking groups include carbon containing linking groups, typically ranging from about 2 to 18, usually from about 2 to 8 carbon atoms, where the carbon containing linking groups may or may not include one or more heteroatoms, e.g. S, O, N etc., and may or may not include one or more sites of unsaturation. Of particular interest in many embodiments are alkyl linking groups, typically lower alkyl linking groups of 1 to 16, usually 1 to 4 carbon atoms, where the linking groups may include one or more sites of unsaturation. The functionalized nucleotides (or primers) used in the above methods of functionalized target generation may be fabricated using known protocols or purchased from commercial vendors, e.g., Sigma, Roche, Ambion, and NEN. Functional groups may be prepared according to ways known to those of skill in the art, including the representative information found in U.S. Pat. Nos. 4,404,289; 4,405,711; 4,337,063; 5,268,486 and Br. Patent 1,529,202, which are all incorporated by reference.

Amine-modified nucleotides are used in several embodiments of the disclosure. The amine-modified nucleotide is a nucleotide that has a reactive amine group for attachment of the label. It is contemplated that any ribonucleotide (G, A, U, or C) or deoxyribonucleotide (G, A, T, or C) can be modified for labeling. Examples include, but are not limited to, the following modified ribo- and deoxyribo-nucleotides: 5-(3-aminoalryl)-UTP; 8-[(4-amino)butyl]-amino-ATP and 8-[(6-amino)butyl]-amino-ATP; N6-(4-amino)butyl-ATP, N6-(6-amino)butyl-ATP, N4-[2,2-oxy-bis-(ethylamine)]-CTP; N6-(6-amino)hexyl-ATP; 8-[(6-amino)hexyl]-amino-ATP; 5-propargylamino-CTP, 5-propargylamino-UTP; 5-(3-aminoallyl)-dUTP; 8-[(4-amino)butyl]-amino-dATP and 8-[(6-amino)butyl]-amino-dATP; N6-(4-amino)butyl-dATP, N6-(6-amino)butyl-dATP, N4-[2,2-oxy-bis-(ethylamine)]-dCTP; N6-(6-amino)hexyl-dATP; 8-[(6-amino)hexyl]-amino-dATP; 5-propargylamino-dCTP, and 5-propargylamino-dUTP. Such nucleotides can be prepared according to methods known to those of skill in the art. Moreover, a person of ordinary skill in the art could prepare other nucleotide entities with the same amine-modification, such as a 5-(3-aminoallyl)-CTP, GTP, ATP, dCTP, dGTP, dTTP, or dUTP in place of a 5-(3-aminoallyl)-UTP.

G. Preparation of Nucleic Acids

A nucleic acid may be made by any technique known to one of ordinary skill in the art, such as for example, chemical synthesis, enzymatic production or biological production. In some embodiments, siRNA compositions of the disclosure are chemically synthesized.

Nucleic acid synthesis is performed according to standard methods. Additionally, U.S. Pat. Nos. 4,704,362, 5,221,619, and 5,583,013 each describe various methods of preparing synthetic nucleic acids. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by (Froehler et al., 1986) and U.S. Pat. No. 5,705,629, each incorporated herein by reference. In the methods of the present disclosure, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. Nos. 4,683,202 and 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al., 1989, incorporated herein by reference).

Chemical oligonucleotide synthesis is well known to those of skill in the art. Various different mechanisms of oligonucleotide synthesis have been disclosed in, for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference. Basically, chemical synthesis can be achieved by the diester method, the triester method, polynucleotide phosphorylase method, and by solid-phase chemistry. These methods are discussed in further detail below.

Diester method. The diester method was the first to be developed to a usable state, primarily by Khorana and co-workers. (Khorana, 1979). The basic step is the joining of two suitably protected deoxynucleotides to form a dideoxynucleotide containing a phosphodiester bond. The diester method is well established and has been used to synthesize DNA molecules (Khorana, 1979).

Triester method. The main difference between the diester and triester methods is the presence in the latter of an extra protecting group on the phosphate atoms of the reactants and products (Itakura et al., 1975). The phosphate protecting group is usually a chlorophenyl group, which renders the nucleotides and polynucleotide intermediates soluble in organic solvents. Therefore purifications are done in chloroform solutions. Other improvements in the method include: (i) the block coupling of trimers and larger oligomers, (ii) the extensive use of high-performance liquid chromatography for the purification of both intermediate and final products, and (iii) solid-phase synthesis.

Polynucleotide phosphorylase method. This is an enzymatic method of DNA synthesis that can be used to synthesize many useful oligonucleotides (Gillam et al., 1978). Under controled conditions, polynucleotide phosphorylase adds predominantly a single nucleotide to a short oligonucleotide. Chromatographic purification allows the desired single adduct to be obtained. At least a trimer is required to start the procedure, and this primer must be obtained by some other method. The polynucleotide phosphorylase method works and has the advantage that the procedures involved are familiar to most biochemists.

Solid-phase methods. Drawing on the technology developed for the solid-phase synthesis of polypeptides, it has been possible to attach the initial nucleotide to solid support material and proceed with the stepwise addition of nucleotides. All mixing and washing steps are simplified, and the procedure becomes amenable to automation. These syntheses are now routinely carried out using automatic nucleic acid synthesizers.

Phosphoramidite chemistry (Beaucage and Lyer, 1992) has become by far the most widely used coupling chemistry for the synthesis of oligonucleotides. As is well known to those skilled in the art, phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain (generally anchored at one end to a suitable solid support) to form the oligonucleotide product.

Recombinant methods. Recombinant methods for producing nucleic acids in a cell are well known to those of skill in the art. These include the use of vectors (viral and non-viral), plasmids, cosmids, and other vehicles for delivering a nucleic acid to a cell, which may be the target cell or simply a host cell (to produce large quantities of the desired RNA molecule). Alternatively, such vehicles can be used in the context of a cell-free system so long as the reagents for generating the RNA molecule are present. Such methods include those described in Sambrook (2003; 2001; 1989), which are hereby incorporated by reference.

The siRNA can be obtained by preparing a recombinant version thereof (i.e., by using the techniques of genetic engineering to produce a recombinant nucleic acid which can then be isolated or purified by techniques well known to one of ordinary skill in the art). This embodiment involves growing a culture of host cells in a suitable culture medium, and purifying the siRNA from the cells or the culture in which the cells are grown. For example, the methods include a process for producing a siRNA in which a host cell containing a suitable expression vector that includes a nucleic acid encoding an siRNA is cultured under conditions that allow expression of the encoded siRNA. The siRNA can be recovered from the culture, from the culture medium or from a lysate prepared from the host cells, and further purified. The host cell can be a higher eukaryotic host cell such as a mammalian cell, a lower eukaryotic host cell such as a yeast cell, or the host cell can be a prokaryotic cell such as a bacterial cell. Introduction of a vector containing the nucleic acid encoding the siRNA into the host cell can be effected by calcium phosphate transfection, DEAE, dextran-mediated transfection, lipid-mediated transfection, or electroporation (Davis, L. et al., Basic Methods in Molecular Biology (1986)).

Any host/vector system can be used to express one or more of the siRNAs. These include, but are not limited to, eukaryotic hosts such as HeLa cells and yeast, as well as prokaryotic host such as *E. coli* and *B. subtilis*. siRNA can be expressed in mammalian cells, yeast, bacteria, or other cells where the siRNA gene is under the control of an appropriate promoter. Appropriate cloning and expression vectors for use with prokaryotic and eukaryotic hosts are described by Sambrook, et al., in Molecular Cloning: A Laboratory Manual, Second Edition, Cold Spring Harbor, N.Y. (1989). In the preferred embodiment, the siRNA is expressed in mammalian cells. Examples of mammalian expression systems include C127, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells. Mammalian expression vectors will comprise an origin of replication, a suitable promoter, polyadenylation site, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements. Potentially suitable yeast strains include *Saccharomyces cerevisiae, Schizosaccharomyces pombe, Kluyveromyces* strains, *Candida*, or any yeast strain capable of expressing siRNA. Potentially suitable bacterial strains include *Escherichia coli, Bacillus subtilis, Salmonella typhimurium*, or any bacterial strain capable of expressing siRNA.

The siRNA may be prepared by culturing transformed host cells under culture conditions suitable to express the siRNA. The resulting expressed siRNA may then be purified from such cultures (i.e., from culture medium or cell extracts) using known purification processes, such as gel filtration and ion exchange chromatography. The purification of the siRNA may also include an affinity column containing agents which will bind to the protein; one or more column steps over such affinity resins as concanavalin A-agarose, Heparin-Toyopearl™ or Cibacrom blue 3GA Sepharose™; one or more steps involving hydrophobic interaction chromatography using such resins as phenyl ether, butyl ether, or propyl ether; immunoaffinity chromatography, or complementary cDNA affinity chromatography.

In a preferred embodiment, the siRNA can be obtained synthetically, for example, by chemically synthesizing a nucleic acid by any method of synthesis known to the skilled artisan. The synthesized siRNA can then be purified by any method known in the art. Methods for chemical synthesis of nucleic acids include, but are not limited to, in vitro chemical synthesis using phosphotriester, phosphate or phosphoramidite chemistry and solid phase techniques, or via deoxynucleoside H-phosphonate intermediates (see U.S. Pat. No. 5,705,629 to Bhongle).

In some circumstances, for example, where increased nuclease stability is desired, nucleic acids having nucleic acid analogs and/or modified internucleoside linkages may be preferred. Nucleic acids containing modified internucleoside linkages may also be synthesized using reagents and methods that are well known in the art. For example, methods of synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide ($-CH_2-S-CH_2$), dimethylene-sulfoxide ($-CH_2-SO-CH_2$), dimethylene-sulfone ($-CH_2-SO_2-CH_2$), 2'-O-alkyl, and 2'-deoxy-2'-fluoro phosphorothioate internucleoside linkages are well known in the art (see Uhlmann et al., 1990, Chem. Rev. 90:543-584; Schneider et al., 1990, Tetrahedron Lett. 31:335 and references cited therein). U.S. Pat. Nos. 5,614,617 and 5,223,618 to Cook, et al., U.S. Pat. No. 5,714,606 to Acevedo, et al., U.S. Pat. No. 5,378,825 to Cook, et al., U.S. Pat. Nos. 5,672,697 and 5,466,786 to Buhr, et al., U.S. Pat. No. 5,777,092 to Cook, et al., U.S. Pat. No. 5,602,240 to De Mesmaeker, et al., U.S. Pat. No. 5,610,289 to Cook, et al. and U.S. Pat. No. 5,858,988 to Wang, also describe nucleic acid analogs for enhanced nuclease stability and cellular uptake.

The inventors contemplate siRNAs substituted with locked nucleic acids (LNAs). LNA nucleotides (also termed (β-D-Methyleneoxy (4'-$CH_2$—O-2') BNA) are constrained by a bond between the 2' and 4' positions of the ribose ring (FIG. 8). This constraint "locks" the nucleotide into a position that is ideal for base-pairing and the introduction of a handful of LNA nucleotides into an siRNA can tailor the affinity of an siRNA for optimal success in many applications.

H. Isolation of Nucleic Acids

Nucleic acids may be isolated using techniques well known to those of skill in the art, though in particular embodiments, methods for isolating small nucleic acid molecules and/or isolating RNA molecules can be employed. Chromatography is a process often used to separate or isolate nucleic acids from protein or from other nucleic acids. Such methods can involve electrophoresis with a gel matrix, filter columns, alcohol precipitation, and/or other chromatography. If siRNA from cells is to be used or evaluated, methods generally involve lysing the cells with a chaotropic (e.g., guanidinium isothiocyanate) and/or detergent (e.g., N-lauroyl sarcosine) prior to implementing processes for isolating particular populations of RNA.

In particular methods for separating siRNA from other nucleic acids, a gel matrix is prepared using polyacrylamide, though agarose can also be used. The gels may be graded by concentration or they may be uniform. Plates or tubing can be used to hold the gel matrix for electrophoresis. Usually one-dimensional electrophoresis is employed for the separation of nucleic acids. Plates are used to prepare a slab gel, while the tubing (glass or rubber, typically) can be used to prepare a tube gel. The phrase "tube electrophoresis" refers to the use of a tube or tubing, instead of plates, to form the gel. Materials for implementing tube electrophoresis can be readily prepared by a person of skill in the art or purchased, such as from C.B.S. Scientific Co., Inc. or Scie-Plas.

IV. Cancer Treatment

A. Cancers

Cancers that may be treated or prevented by methods and compositions of the disclosure include cancer cells from the bladder, blood, bone, bone marrow, brain, breast, colon, esophagus, gastrointestine, gum, head, kidney, liver, lung, nasopharynx, neck, ovary, prostate, salivary gland, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma with squamous metaplasia; thymoma, malignant; ovarian stromal tumor, malignant; thecoma, malignant; granulosa cell tumor, malignant; androblastoma, malignant; Sertoli cell carcinoma; leydig cell tumor, malignant; lipid cell rumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. Moreover, siRNA can be utilized in a primary tumor or a metastasized tumor.

Of particular interest in the present disclosure is liver cancer, also known as hepatic cancer. Liver tumors are discovered on medical imaging equipment (often by accident) or present themselves symptomatically as an abdominal mass, abdominal pain, yellow skin, nausea or liver dysfunction. The leading cause of liver cancer is cirrhosis due to either hepatitis B, hepatitis C, or alcohol. In 2013, 300,000 deaths from liver cancer were due to hepatitis B, 343,000 to hepatitis C and 92,000 to alcohol. Liver cancers are not the same as liver metastases, which start in another part of the body and spread to the liver. Liver cancers are formed from either the liver itself or from structures within the liver, including blood vessels or the bile duct.

Primary liver cancer is globally the sixth most frequent cancer, and the second leading cause of cancer death. In 2012 it occurred in 782,000 people and resulted in 746,000 deaths. Higher rates of liver cancer occur where hepatitis B and C are common, including East-Asia and sub-Saharan Africa. Five year survival rates are 17% in the United States. hepatocellular carcinoma (HCC). HCC is a cancer formed by liver cells, known as hepatocytes, that become malignant. Another type of cancer formed by liver cells is hepatoblastoma, which is specifically formed by immature liver cells. It is a rare malignant tumor that primarily develops in children, and accounts for approximately 1% of all cancers in children and 79% of all primary liver cancers under the age of 15. Most hepatoblastomas form in the right lobe.

Liver cancer can also form from other structures within the liver such as the bile duct, blood vessels and immune cells. Cancer of the bile duct (cholangiocarcinoma and cholangiocellular cystadenocarcinoma) account for approximately 6% of primary liver cancers. There is also a variant type of HCC that consists of both HCC and cholangiocarcinoma. Tumors of the blood vessels (angiosarcoma and hemangioendothelioma, embryonal sarcoma and fibrosarcoma are produced from a type of connective tissue known as mesenchyme. Cancers produced from muscle in the liver are leiomyosarcoma and rhabdomyosarcoma. Other less common liver cancers include carcinosarcomas, teratomas, yolk sac tumours, carcinoid tumours and lymphomas. Lymphomas usually have diffuse infiltration to liver, but it may also form a liver mass in rare occasions.

Many cancers found within the liver are not true liver cancers, but are cancers from other sites in the body that have spread to the liver (known as metastases). Frequently, the site of origin is the gastrointestinal tract (such as colon cancer and carcinoid tumors mainly of the appendix), but also from breast cancer, ovarian cancer, lung cancer, renal cancer, prostate cancer.

Because liver cancer is an umbrella term for many types of cancer, the signs and symptoms depend on what type of cancer is present. Cholangiocarcinoma is associated with sweating, jaundice, abdominal pain, weight loss and liver enlargement. Hepatocellular carcinoma is associated with abdominal mass, abdominal pain, emesis, anemia, back pain, jaundice, itching, weight loss and fever.

Viral infection with either hepatitis C virus (HCV) or Hepatitis B virus (HBV) is the chief cause of liver cancer in the world today, accounting for 80% of hepatocellular carcinoma (HCC). The viruses cause HCC because massive inflammation, fibrosis and eventual cirrhosis occurs within the liver. HCC usually arises after cirrhosis, with an annual incidence of 1.7% in cirrhotic HCV-infected individuals. Around 5-10% of individuals that become infected with HBV become chronic carriers, and around 30% of these acquire chronic liver disease, which can lead to HCC. HBV infection is also linked to cholangiocarcinoma. The role of viruses other than HCV or HBV in liver cancer is much less clear, although there is some evidence that co-infection of HBV and hepatitis D virus may increase the risk of HCC.

Many genetic and epigenetic changes are formed in liver cells during HCV and HBV infection, which is a major factor in the production of the liver tumours. The viruses induce malignant changes in cells by altering gene methylation, affecting gene expression and promoting or repressing cellular signal transduction pathways. By doing this the viruses can prevent cells from undergoing a programmed form of cell death (apoptosis) and promote viral replication and persistence.

In addition to virus-related cirrhosis described above, other causes of cirrhosis can lead to HCC. Alcohol intake correlates with risk of HCC, and the risk is far greater in individuals with an alcohol-induced cirrhotic liver. There are a few disorders that are known to cause cirrhosis and lead to cancer, including hereditary hemochromatosis and primary biliary cirrhosis.

Aflatoxin exposure can lead to the development of HCC. The aflatoxins are a group of chemicals produced by the fungi *Aspergillus flavus* (the name comes from *A. flavus* toxin) and *A. parasiticus*. Food contamination by the fungi leads to ingestion of the chemicals, which are very toxic to the liver. Common foodstuffs contaminated with the toxins are cereals, peanuts and other vegetables. Contamination of food is common in Africa, South-East Asia and China. Concurrent HBV infection and aflatoxin exposure increases the risk of liver cancer to over three times that seen in HBV infected individuals without aflatoxin exposure. The mechanism by which aflatoxins cause cancer is through genetic mutation of a gene required for the prevention of cancer: p53.

Other causes in adults include:

High grade dysplastic nodules are precancerous lesions of the liver. Within 2 years, there is a risk of cancer arising from these nodules of 30-40%.

Obesity has emerged as an important risk factor as it can lead to steatohepatitis.

Diabetes increases the risk of HCC.

Smoking increases the risk of HCC compared to non-smokers and previous smokers.

There is around 5-10% lifetime risk of cholangiocarcinoma in people with primary sclerosing cholangitis.

Liver fluke infection increases the risk of cholangiocarcinoma, and is the reason Thailand has particularly high rates of this cancer.

Increased risk of liver cancer in children can be caused by Beckwith-Wiedemann Syndrome (associated with hepatoblastoma), familial adenomatous polyposis (associated with hepatoblastoma), low birth weight (associated with hepatoblastoma), Progressive familial intrahepatic cholestasis (associated with HCC) and Trisomy 18 (associated with hepatoblastoma).

Many imaging modalities are used to aid in the diagnosis of primary liver cancer. For HCC these include sonography (ultrasound), computed tomography (CT) and magnetic resonance imaging (MRI). When imaging the liver with ultrasound, a mass greater than 2 cm has more than 95% chance of being HCC. The majority of cholangiocarcimas occur in the hilar region of the liver, and often present as bile duct obstruction. If the cause of obstruction is suspected to be malignant, endoscopic retrograde cholangiopancreatography (ERCP), ultrasound, CT, MRI and magnetic resonance cholangiopancreatography (MRCP) are used.

Tumor markers, chemicals sometimes found in the blood of people with cancer, can be helpful in diagnosing and monitoring the course of liver cancers. High levels of alpha-fetoprotein (AFP) in the blood can be found in many cases of HCC and intrahepatic cholangiocarcinoma. Cholangiocarcinoma can be detected with these commonly used tumor markers: carbohydrate antigen 19-9 (CA 19-9), carcinoembryonic antigen (CEA) and cancer antigen 125 (CA125). These tumour markers are found in primary liver cancers, as well as in other cancers and certain other disorders.

Surgical resection is often the treatment of choice for non-cirrhotic livers. Increased risk of complications such as liver failure can occur with resection of cirrhotic livers. 5-year survival rates after resection has massively improved over the last few decades and can now exceed 50%. Recurrence rates after resection due to the spread of the initial tumor or formation of new tumors exceeds 70%. Liver transplantation can also be used in cases of HCC where this form of treatment can be tolerated and the tumor fits specific criteria (such as the Milan criteria). Less than 30-40% of individuals with HCC are eligible for surgery and transplant because the cancer is often detected late stage. Also, HCC can progress during the waiting time for liver transplants, which can prevent transplant due to the strict criteria.

Percutaneous ablation is the only non-surgical treatment that can offer cure. There are many forms of percutaneous ablation, which consist of either injecting chemicals into the liver (ethanol or acetic acid) or producing extremes of temperature using radio frequency ablation, microwaves, lasers or cryotherapy. Of these, radio frequency ablation has one of the best reputations in HCC, but the limitations include inability to treat tumors close to other organs and blood vessels due to heat generation and the heat sync effect, respectively.

Systemic chemotherapeutics are not routinely used in HCC, although local chemotherapy may be used in a procedure known as transarterial chemoembolization. In this procedure, cytotoxic drugs such as doxorubicin or cisplatin with lipiodol are administered and the arteries supplying the liver are blocked by gelatin sponge or other particles. Because most systemic drugs have no efficacy in the treatment of HCC, research into the molecular pathways involved in the production of liver cancer produced sorafenib, a targeted therapy drug that prevents cell proliferation and blood cell growth. This drug provides a survival benefit for advanced HCC.

Radiotherapy is not often used in HCC because the liver is not tolerant to radiation. Although with modern technology it is possible to provide well targeted radiation to the tumor, minimizing the dose to the rest of the liver. Dual treatments of radiotherapy plus chemoembolization, local chemotherapy, systemic chemotherapy or targeted therapy drugs may show benefit over radiotherapy alone.

Resection is an option in cholangiocarcinoma, but less than 30% of cases of cholangiocarcinoma are resectable at diagnosis. After surgery, recurrence rates are up to 60%. Liver transplant may be used where partial resection is not an option, and adjuvant chemoradiation may benefit some cases.

60% of cholangiocarcinomas form in the perihilar region and photodynamic therapy can be used to improve quality of life and survival time in these unresectable cases. Photodynamic therapy is a novel treatment that utilizes light activated molecules to treat the tumor. The compounds are activated in the tumor region by laser light, which causes the release of toxic reactive oxygen species, killing tumor cells.

Systemic chemotherapies such as gemcitabine and cisplatin are sometimes used in inoperable cases of cholangiocarcinoma. Radio frequency ablation, transarterial chemoembolization and internal radiotherapy (brachytherapy) all show promise in the treatment of cholangiocarcinoma. Radiotherapy may be used in the adjuvant setting or for palliative treatment of cholangiocarcinoma.

Removing the tumor by either surgical resection or liver transplant can be used in the treatment of hepatoblastoma. In some cases surgery can offer a cure. Chemotherapy may be used before and after surgery and transplant. Chemotherapy, including cisplatin, vincristine, cyclophosphamide, and doxorubicin are used for the systemic treatment of hepatoblastoma. Out of these drugs, cisplatin seems to be the most effective.

B. Combination Therapy

In order to increase the effectiveness of a siRNA composition, it may be desirable to combine these compositions with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, decreasing metabolic activity, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell, which amounts may be less than required for monotherapy efficacy.

This process may involve contacting the cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s). Alternatively, one agent may precede or follow the other by intervals ranging from minutes to weeks. In embodiments where the agents are applied separately to the subject, one would generally ensure that a significant period of time did not expire between the time of each delivery, such that the agents would still be able to exert an advantageously combined effect on the subject. In such instances, it is contemplated that one may contact the subject with both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

In the context of the present disclosure, it is contemplated that siRNA therapy could be used similarly in conjunction with chemotherapeutic, radiotherapeutic, or immunotherapeutic intervention, in addition to other pro-apoptotic or cell cycle regulating agents. It is expected that the treatment cycles would be repeated as necessary. It also is contemplated that various standard therapies, as well as surgical intervention, may be applied in combination with the described therapy. Exemplary additional therapies include surgery, chemotherapy, radiation, hormone therapy, immunotherapy, and or a combination thereof.

Various combinations may be employed, the siRNA is "A" and the other agent or therapy is "B":

| | | | | | |
|---|---|---|---|---|---|
| A/B/A | B/A/B | B/B/A | A/A/B | A/B/B | B/A/A |
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

Administration protocols and formulation of such agents will generally follow those of standard pharmaceutical drugs, as discussed further below.

Chemotherapy. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I; dynemicin, including dynemicin A uncialamycin and derivatives thereof; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin;

losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and docetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylomithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristin, vinblastin and methotrexate and pharmaceutically acceptable salts, acids or derivatives of any of the above.

Radiotherapy. Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present disclosure may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and may be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

Immunotherapy. In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor cell must bear some marker that is amenable to targeting, i.e., is not present on the majority of other cells. Many tumor markers exist and any of these may be suitable for targeting in the context of the present disclosure. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds may be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739,169; Hui and Hashimoto, 1998; Christodoulides et al., 1998), cytokine therapy, e.g., interferons α, β, and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

Surgery. Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present disclosure, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present disclosure may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

In some particular embodiments, after removal of the tumor, an adjuvant treatment with a compound of the present disclosure is believe to be particularly efficacious in reducing the reoccurance of the tumor. Additionally, the compounds of the present disclosure can also be used in a neoadjuvant setting.

It also should be pointed out that any of the foregoing therapies may prove useful by themselves in treating cancer.

C. Methods of Treatment

Methods for treatment or prevention of at least one symptom or manifestation of cancer are provided including administration of an effective amount of a composition containing a nucleic acid molecule to alleviate at least one symptom or decrease at least one manifestation. In a preferred embodiment, the cancer is liver cancer. The compositions described herein can be administered in effective dosages alone, in combination with other siRNAs, or in combination with adjuvant cancer therapy such as surgery, chemotherapy, radiotherapy, thermotherapy, immunotherapy, hormone therapy and laser therapy, to provide a beneficial effect, e.g. reduce tumor size, reduce cell proliferation of the tumor, inhibit angiogenesis, inhibit metastasis, or otherwise improve at least one symptom or manifestation of the disease.

The compositions are administered to an individual in need of treatment of at least one symptom or manifestation (since disease can occur/progress in the absence of symptoms) of cancer. The individual may be at risk for cancer, such as having personal or family history, be a tobacco user, have genetic marker(s) and so forth. In some cases, the therapy acts as a radiation or chemotherapy sensitizer, for example. The compositions described herein can be administered to a subject prior to administration of a cytotoxic therapy in an amount effective to sensitize cells or tissues to be treated to the effects of the cytotoxic therapy. In one embodiment the cytotoxic therapy is radiotherapy. In another embodiment the cytotoxic therapy is chemotherapy. Sensitization describes a condition of the cells or tissues to be treated in which prior administration of the compositions described herein increases at least one effect of the cytotoxic therapy on the cells or tissues relative to cells or tissues not receiving prior administration of the compositions described herein. The increased effect may be on reduction of tumor size, reduction in cell proliferation of a tumor, inhibition of angiogenesis, inhibition of metastasis, or improvement of at least one symptom or manifestation of the disease.

D. Method of Administration

In general, methods of administering nucleic acids are well known in the art. In particular, the routes of administration already in use for nucleic acid therapeutics, along with formulations in current use, provide preferred routes of administration and formulation for the nucleic acids described above.

Nucleic acid compositions can be administered by a number of routes including, but not limited to oral, intravenous, intraperitoneal, intramuscular, transdermal, subcutaneous, topical, sublingual, or rectal means. Nucleic acids can also be administered via liposomes or nanoparticles. Such administration routes and appropriate formulations are generally known to those of skill in the art.

Administration of the formulations described herein may be accomplished by any acceptable method that allows the siRNA or nucleic acid encoding the siRNA to reach its target. The particular mode selected will depend of course, upon exemplary factors such as the particular formulation, the severity of the state of the subject being treated, and the dosage required for therapeutic efficacy. As generally used herein, an "effective amount" of a nucleic acid is the amount that is able to treat one or more symptoms of cancer or related disease, reverse the progression of one or more symptoms of cancer or related disease, halt the progression of one or more symptoms of cancer or related disease, or prevent the occurrence of one or more symptoms of cancer or related disease in a subject to whom the formulation is administered, as compared to a matched subject not receiving the compound or therapeutic agent. The actual effective amounts of drug can vary according to the specific drug or combination thereof being utilized, the particular composition formulated, the mode of administration, and the age, weight, condition of the patient, and severity of the symptoms or condition being treated.

Any acceptable method known to one of ordinary skill in the art may be used to administer a formulation to the subject. The administration may be localized (i.e., to a particular region, physiological system, tissue, organ, or cell type) or systemic, depending on the condition being treated.

Injections can be, e.g., intravenous, intratumoral, intrahepatic, intradermal, subcutaneous, intramuscular, or intraperitoneal. The composition can be injected intradermally for treatment or prevention of cancer, for example. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. Inhalation includes administering the composition with an aerosol in an inhaler, either alone or attached to a carrier that can be absorbed. For systemic administration, it may be preferred that the composition is encapsulated in liposomes.

Preferably, the agent and/or nucleic acid delivery system are provided in a manner which enables tissue-specific uptake of the agent and/or nucleic acid delivery system. Techniques include using tissue or organ localizing devices, such as wound dressings or transdermal delivery systems, using invasive devices such as vascular or urinary catheters, and using interventional devices such as stents having drug delivery capability and configured as expansive devices or stent grafts.

The formulations may be delivered using a bioerodible implant by way of diffusion or by degradation of the polymeric matrix. In certain embodiments, the administration of the formulation may be designed so as to result in sequential exposures to the siRNA over a certain time period, for example, hours, days, weeks, months or years. This may be accomplished, for example, by repeated administrations of a formulation or by a sustained or controlled release delivery system in which the siRNA is delivered over a prolonged period without repeated administrations. Administration of the formulations using such a delivery system may be, for example, by oral dosage forms, bolus injections, transdermal patches or subcutaneous implants. Maintaining a substantially constant concentration of the composition may be preferred in some cases.

Other delivery systems suitable include, but are not limited to, time-release, delayed release, sustained release, or controlled release delivery systems. Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing nucleic acids are described in, for example, U.S. Pat. No. 5,075,109. Other examples include nonpolymer systems that are lipid-based including sterols such as cholesterol, cholesterol esters, and fatty acids or neutral fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include, but are not limited to, erosional systems in which the siRNA is contained in a formulation within a matrix (for example, as described in U.S. Pat. Nos. 4,452,775, 4,675,189, 5,736,152, 4,667,013, 4,748,034 and 5,239,660), or diffusional systems in which an active component controls the release rate (for example, as described in U.S. Pat. Nos. 3,832,253, 3,854,480, 5,133,974 and 5,407,686). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the siRNA. In addition, a pump-based hardware delivery system may be used to deliver one or more embodiments.

Examples of systems in which release occurs in bursts includes, e.g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapsule core degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be e.g., in the form of pellets, or capsules.

Use of a long-term release implant may be particularly suitable in some embodiments. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

Dosages for a particular patient can be determined by one of ordinary skill in the art using conventional considerations, (e.g., by means of an appropriate, conventional pharmacological protocol). A physician may, for example, prescribe a relatively low dose at first, subsequently increasing the dose until an appropriate response is obtained. The dose-administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of the siRNA employed and the condition of the patient, as well as the body weight or surface area of the patient to be treated. The size of the dose is also determined by the existence, nature, and extent of any adverse side-effects that accompany the administration, and formulation, in a particular patient.

Therapeutic compositions comprising one or more nucleic acids are optionally tested in one or more appropriate in vitro and/or in vivo animal models of disease, to confirm efficacy, tissue metabolism, and to estimate dosages, according to methods well known in the art. In particular, dosages can be initially determined by activity, stability or other suitable measures of treatment versus non-treatment (e.g., comparison of treated vs. untreated cells or animal models), in a relevant assay. Formulations are administered at a rate determined by the $LD_{50}$ of the relevant formulation, and/or observation of any side-effects of the nucleic acids at various concentrations, e.g., as applied to the mass and overall health of the patient. Administration can be accomplished via single or divided doses.

In vitro models can be used to determine the effective doses of the nucleic acids as a potential cancer treatment. Suitable in vitro models include, but are not limited to, proliferation assays of cultured tumor cells, growth of cultured tumor cells in soft agar (see Freshney, (1987) Culture of Animal Cells: A Manual of Basic Technique, Wily-Liss, New York, N.Y. Ch 18 and Ch 21), tumor systems in nude mice as described in Giovanella et al., 1974, mobility and invasive potential of tumor cells in Boyden Chamber assays as described in Pilkington et al., 1997, and angiogenesis assays such as induction of vascularization of the chick chorioallantoic membrane or induction of vascular endothelial cell migration as described in Ribatta et al., 1999 and Li et al., 1999, respectively. Suitable tumor cells lines are available, e.g., from American Type Tissue Culture Collection catalogs.

In vivo models are the preferred models to determine the effective doses of nucleic acids described above as potential cancer treatments. Suitable in vivo models include, but are not limited to, mice that carry a mutation in the KRAS oncogene (Lox-Stop-Lox K-Ras$^{G12D}$ mutants, Kras$^{2tm4Tyj}$) available from the National Cancer Institute (NCI) Frederick Mouse Repository. Other mouse models known in the art and that are available include but are not limited to models for gastrointestinal cancer, hematopoietic cancer, lung cancer, mammary gland cancer, nervous system cancer, ovarian cancer, prostate cancer, skin cancer, cervical cancer, oral cancer, and sarcoma cancer (see emice.nci.nih.gov/mouse_models/).

In determining the effective amount of the siRNA to be administered in the treatment or prophylaxis of disease the physician evaluates circulating plasma levels, formulation toxicities, and progression of the disease.

The dose administered to a 70 kilogram patient is typically in the range equivalent to dosages of currently-used therapeutic antisense oligonucleotides such as Vitravene® (fomivirsen sodium injection) which is approved by the FDA for treatment of cytomegaloviral RNA, adjusted for the altered activity or serum half-life of the relevant composition.

V. Kits of the Disclosure

Kits are also included as part of the disclosure. Kits for implementing methods of the disclosure described herein are specifically contemplated. In some embodiments, there are kits for treating and/or preventing cancer. In some embodiments, a kit comprises in suitable container means, one or more of the following: 1) siRNA; 2) poly(A) polymerase and/or nucleotides (G, A, T, C, and/or U); 3) poly(A) polymerase buffer; reaction buffer; 4) solutions for preparing, isolating, enriching, and/or purifying siRNAs. Other reagents include those generally used for manipulating RNA, such as formamide, loading dye, ribonuclease inhibitors, and DNase. Buffers, as well as other solutions, are contemplated to have a pH of about, at least about, or at most about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0 or more (or any range derivable therein) in certain embodiments of the disclosure. Pharmaceutical carriers for the siRNA composition may or may not be included in the kit.

A reaction buffer for poly(A) polymerase may be included in any kit of the disclosure. Typically, such a poly(A) polymerase reaction buffer includes a volume exclusion reagent, such as PEG, magnesium, and sodium. In certain embodiments, the poly(A) polymerase reaction buffer in the kit contains at least: about 5, 6, 7, 8, 9, 10, 11, 12, 13, 14, 15% or more (or any range derivable therein) PEG; about 5, 10, 15, 20, 25, 30, 35, 40, 45, 50 mM or more MgCl$_2$ (or any range derivable therein); about 100, 200, 300, 400, 500, 600, 700, 800, 900 mM NaCl (or any range derivable therein); about 50, 60, 70, 80, 90, 100, 110, 120, 130, 140, 150 mM or more MES (or any range derivable therein); and about 0.5, 1, 1.5, 2, 2.5, 3, 3.5, 4 mM or more DTT (or any range derivable therein). The kits may also include a manganese source, which may be included as a separate component of a kit or in a solution or buffer with other components, such as in the reaction buffer. It is contemplated that about 5, 10, 15, 20, 25, 30, 35, 40, 45, 50 mM or more of MnCl$_2$ is included in the kit Nucleotides may be for DNA or RNA. Concentrations of a nucleotide or of a nucleotide mix (total concentration of all nucleotides) include, but are not limited to, about, at least about, or at most about 0.5, 1.0, 1 5, 2 0, 2.5, 3.0, 3.5, 4.0, 4.5, 5.0, 5 5, 6.0, 6.5, 7 0, 7.5, 8 0, 8 5, 90, 9 5, 10 0 mM or more (or any range derivable therein). Moreover, they may be modified or not modified. If they are modified, they may have a reactive group or they may have a label attached to it. In certain embodiments, one or more nucleotides in a kit has a reactive group, such as an amine-reactive group. In other embodiments, a nucleotide is already labeled. It may be labeled with a chemiluminescent or fluorecent label, such as a dye. Specifically contemplated are amine-reactive dyes. Moreover, it is specifically contemplated that kits may or may not contain both modified and unmodified nucleotides. Also, kits may contain the label that will be attached to the nucleotide. Any label that can be attached to a nucleotide, as well as any specifically identified herein, can be included in kits of the disclosure.

Individual components may also be provided in a kit in concentrated amounts; in some embodiments, a component is provided individually in the same concentration as it would be in a solution with other components. Concentrations of components may be provided as 1×, 2×, 5×, 10×, or 20× or more.

The components of the kits may be packaged either in aqueous media or in lyophilized form.

The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present disclosure also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred.

However, the components of the kit may be provided as dried powder(s). When reagents and/or components are provided as a dry powder, the powder can be reconstituted by the addition of a suitable solvent. It is envisioned that the solvent may also be provided in another container means.

Such kits may also include components that facilitate isolation of the labeled siRNA. It may also include components that preserve or maintain the siRNA or that protect against its degradation. Such components may be RNase-free or protected against RNases. Such kits generally will comprise, in suitable means, distinct containers for each individual reagent or solution.

A kit will also include instructions for employing the kit components as well the use of any other reagent not included in the kit. Instructions may include variations that can be implemented.

Kits of the disclosure may also include one or more of the following: control RNA; nuclease-free water, RNase-free containers, such as 1.5 mL tubes; RNase-free elution tubes, PEG or dextran, ethanol; acetic acid, sodium acetate; ammonium acetate; guanidimum, detergent; nucleic acid size marker, RNase-free tube tops; and RNase or DNase inhibitors.

It is contemplated that such reagents are embodiments of kits of the disclosure. Such kits, however, are not limited to the particular items identified above and may include any reagent used for the manipulation or characterization of siRNA.

In some embodiments of the disclosure, additional anti-cancer agents are included in the kit. Examples include chemotherapeutics, hormone therapy agents, and immunotherapy agents.

VI. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Figure 1B:
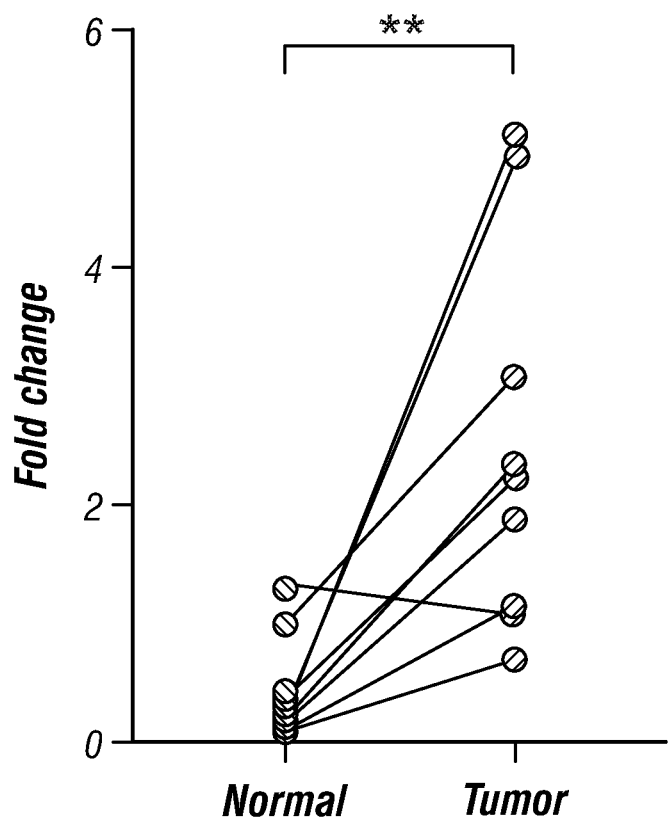

ANLN was overexpressed in human HCC tissues compared to normal liver. An analysis of 35 HCCs and 10 normal liver tissues in the Oncomine database showed that ANLN was expressed about 2-fold higher in HCCs than in normal tissues (FIG. 1A). The inventors also found a similar upregulation of ANLN mRNA in our own collected samples of 9 matching pairs of HCC tissues and normal surrounding liver cells (FIG. 1B). Since ANLN is a key mediator in cytokinesis process, these data indicate the importance of cytokinesis for cancer cells.

Figure 2A:
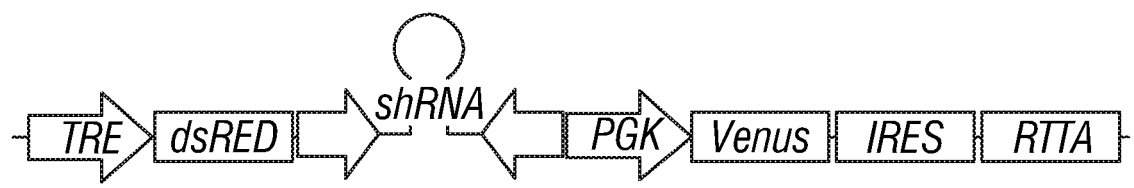
FIGS. 2A-F: Elevated Anln expression is required for cytokinesis.
Figure 2B:
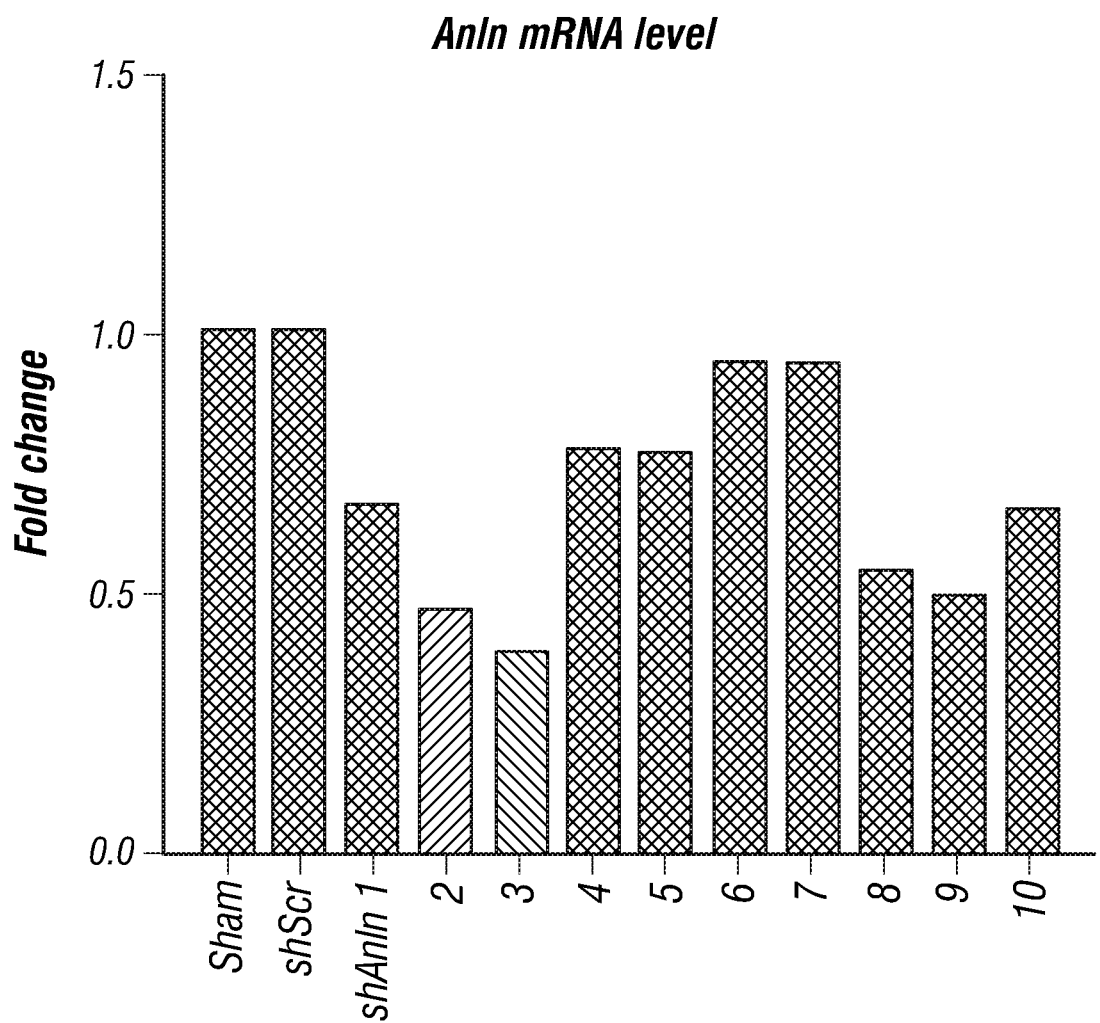
Figure 2C:
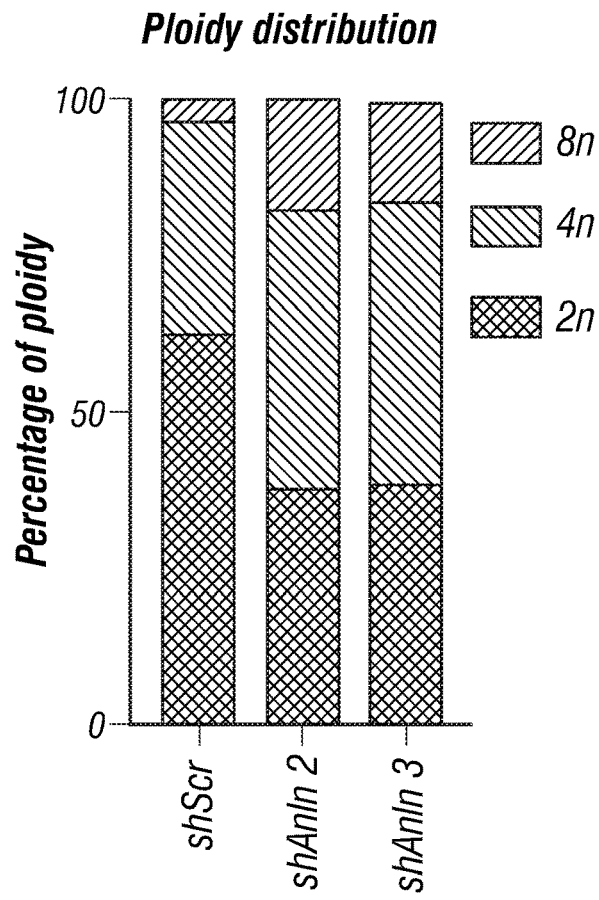
Figure 2D:
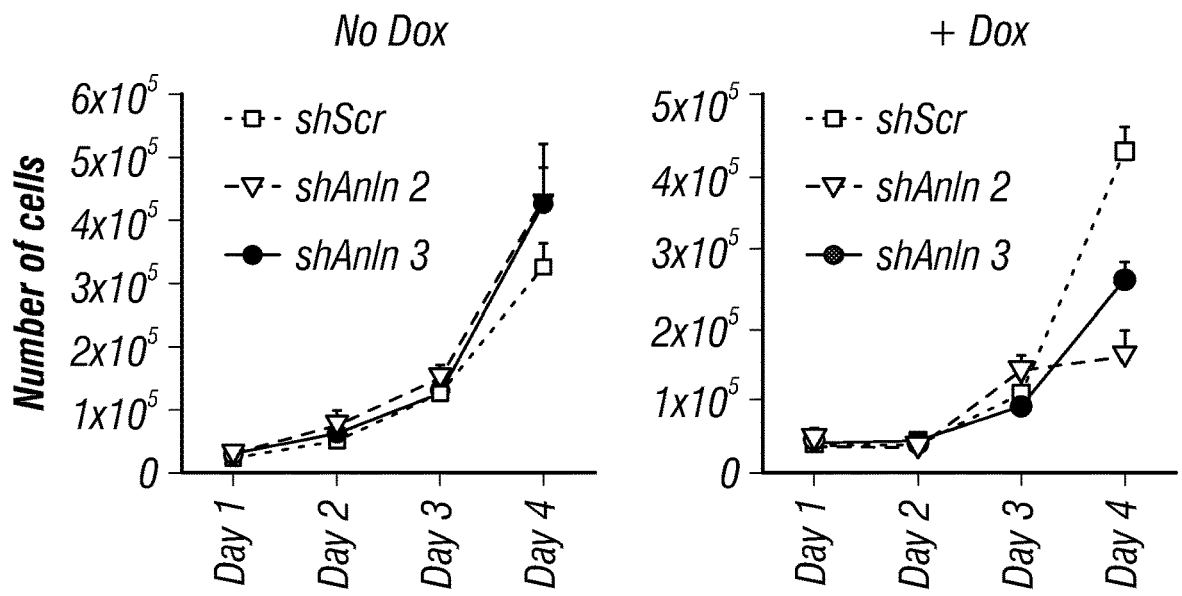
Figure 2E:
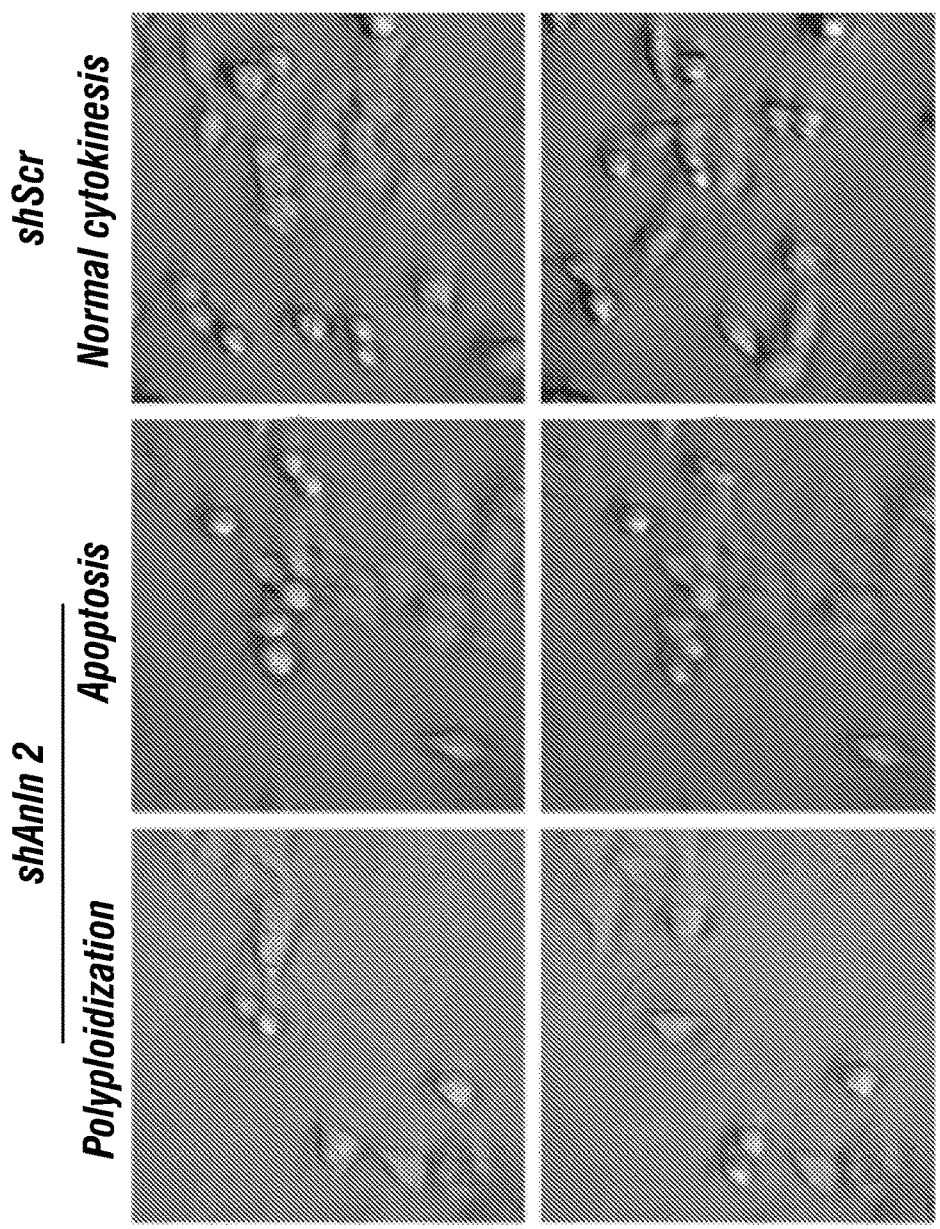
Figure 2F:
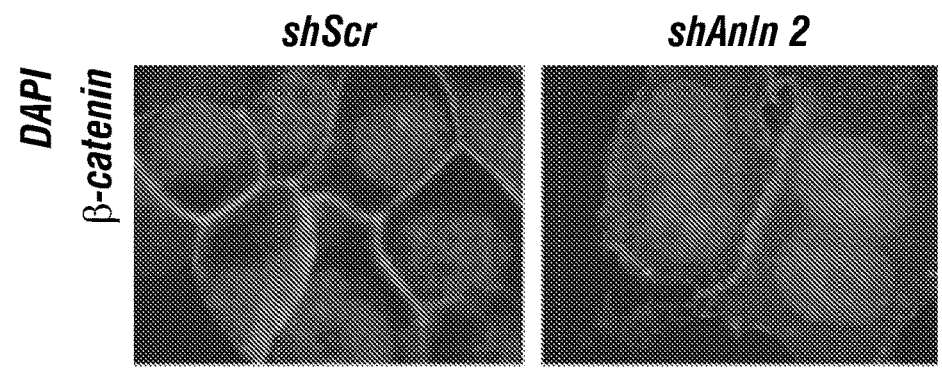

Suppression of Anln impaired cytokinesis and tumor formation of immortalized mouse liver cells. To test whether suppressing ANLN expression is an effective strategy against cytokinesis, the inventors knocked down Anln in H2.35 immortalized mouse cells by infecting the cells with retrovirus containing a Doxycycline (Dox)-inducible Tet-on cassette driving the expression of either scrambled shRNA (shScr) or shRNA against Anln (shAnln) (FIG. 2A, shRNA cassette design from Scott Lowe group, Zuber et al., 2011). After tested 10 distinct Anln shRNAs, the inventors selected shAnln #2 and #3 based on the knockdown efficiency (FIG. 2B). Cells stably infected with shAnln #2 or #3 underwent significant polyploidization after three days of Dox induction (FIG. 2C) and their growth was significantly impaired on the fourth day compared to control cells (FIG. 2D). Live imaging revealed that the cells with Anln knockdown failed to undergo cytokinesis (FIG. 2E) and became multinucleated polyploid cells (FIG. 2F). These data demonstrated that rapid dividing cells require Anln to complete cytokinesis and proliferate.

Figure 3A:
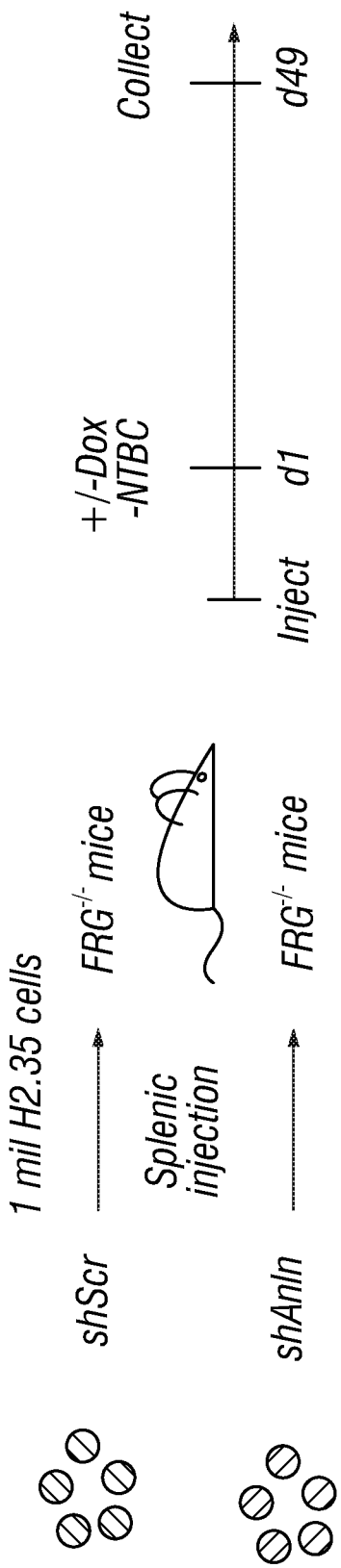
FIGS. 3A-D: Elevated Anln expression is required for tumor formation.
Figures 3B, 3C:
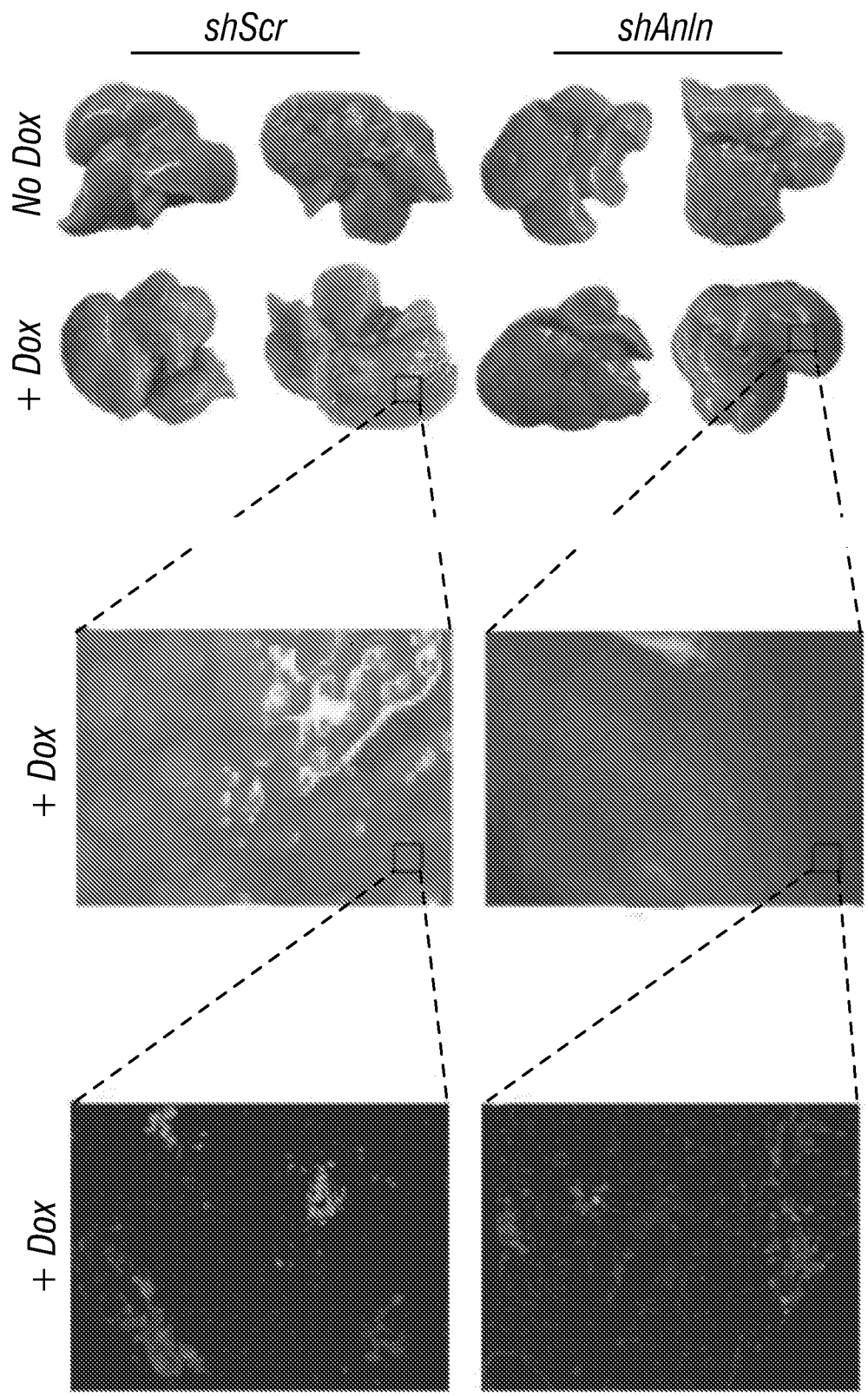
Figure 3D:
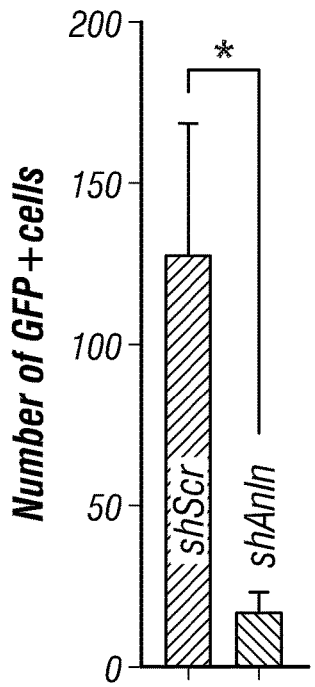

To determine whether impaired cytokinesis inhibits tumor growth in vivo, the inventors generated orthograft tumors using shScr and shAnln infected H2.35 cells via splenic injection into immunosuppressive fumarylacetoacetate hydrolase-deficient (FRG$^{-/-}$) mice (Azuma et al., 2007) (FIG. 3A). These mice are normally maintained under NTBC—containing water, which clears the toxic accumulation of fumarylacetoacetate in the liver. The FRG$^{-/-}$ mouse is a well-established recipient mouse model in which the donor cells are positively selected when NTBC is withdrawn, and the host hepatocytes are negatively selected since they can no longer clear the toxic accumulation of fumarylacetoacetate without NTBC (Azuma et al., 2007; Shafritz, 2007; Grompe and Strom, 2013)). One day after transplanting cells into FRG−/− mice, the inventors withdrew NTBC, and kept half of the shScr and shAnln #3 mice with regular water and the other half with Dox water to induce the shRNAs. Forty-nine days later, they collected the mice and found that for the mice without Dox induction, shScr group and shAnln #3 group had similar tumor burden (FIG. 3B). However, for the mice fed with Dox water, there were significantly fewer tumor nodules in the shAnln #3 group than the shScr group (FIG. 3B). GFP expression from the TRMPVIR construct allowed the inventors to observe clonal expansion of the shScr donor cells compared to that of shAnln donor cells (FIGS. 3C and 3D).

Figure 4A:
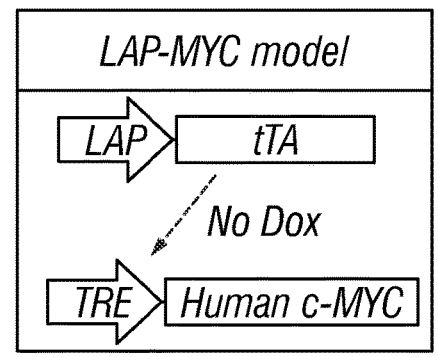
FIGS. 4A-J: Elevated Anln expression is required for MYC-driven liver cancer formation in transgenic mouse model.
Figure 4B:
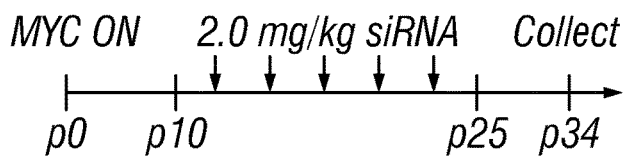
Figure 4C:
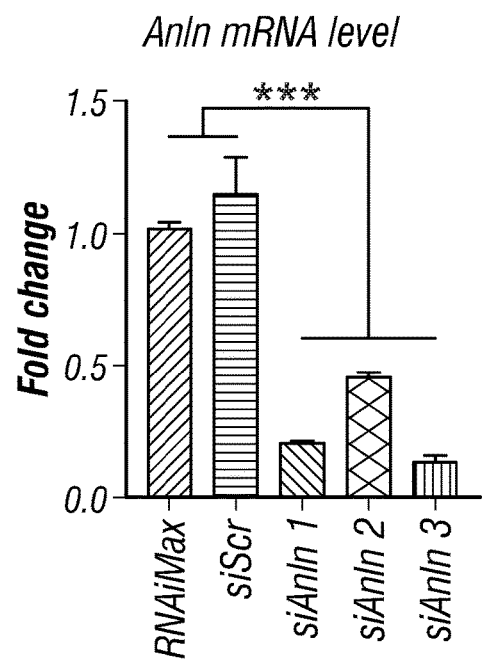
Figure 4D:
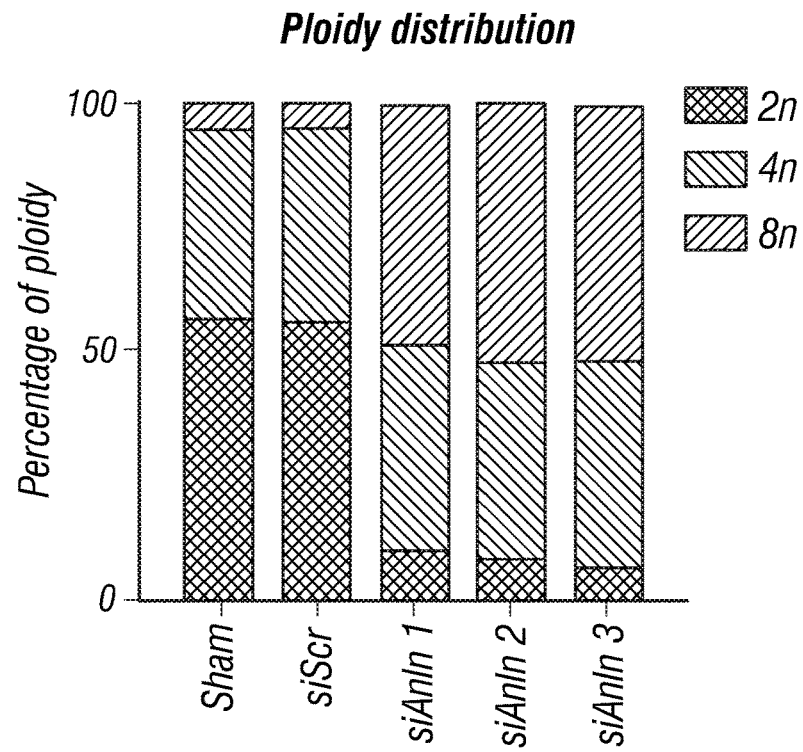
Figure 4E:
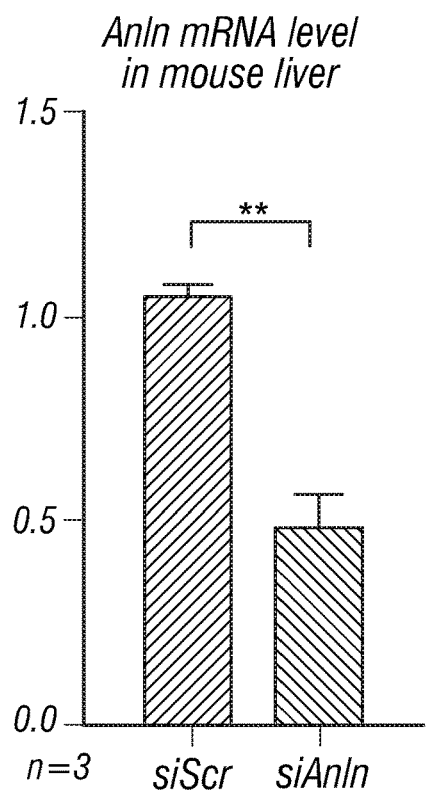
Figure 4F:
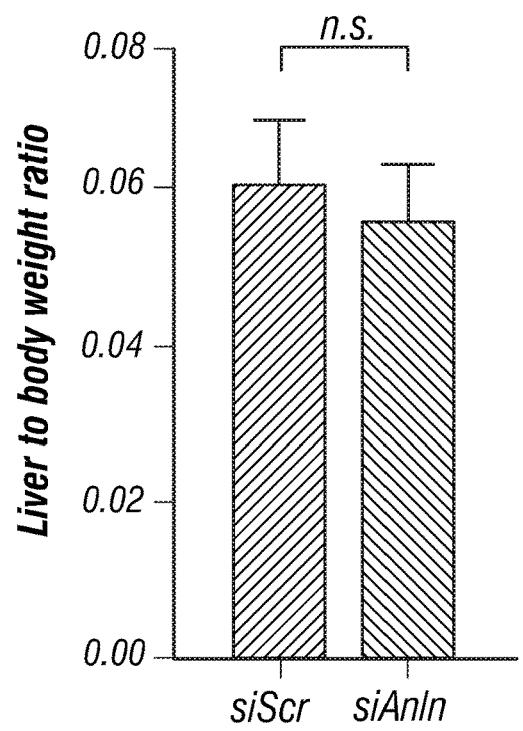
Figure 4G:
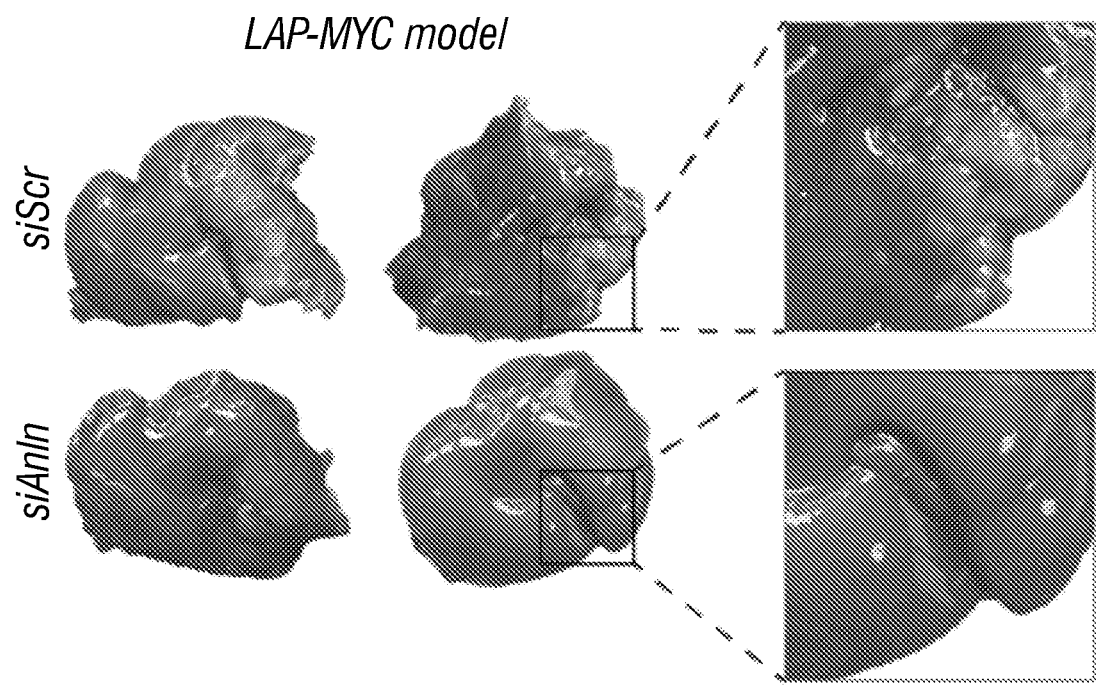
Figure 4H:
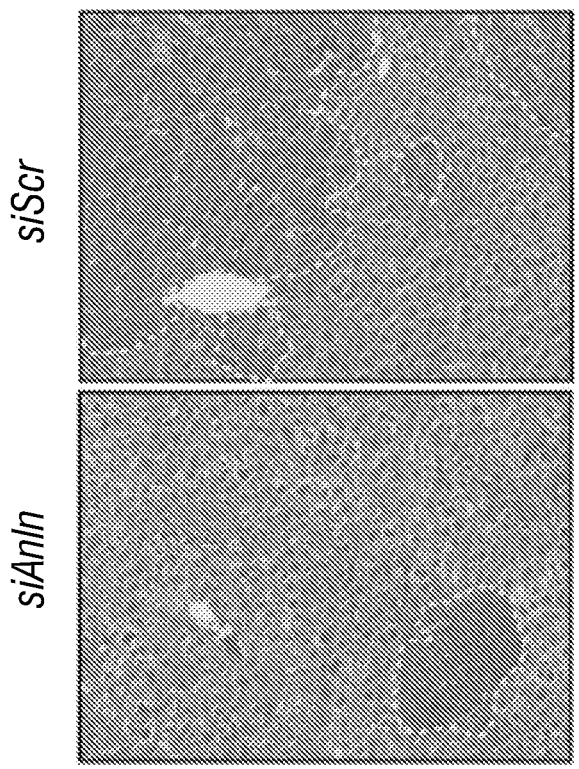
Figure 4I:
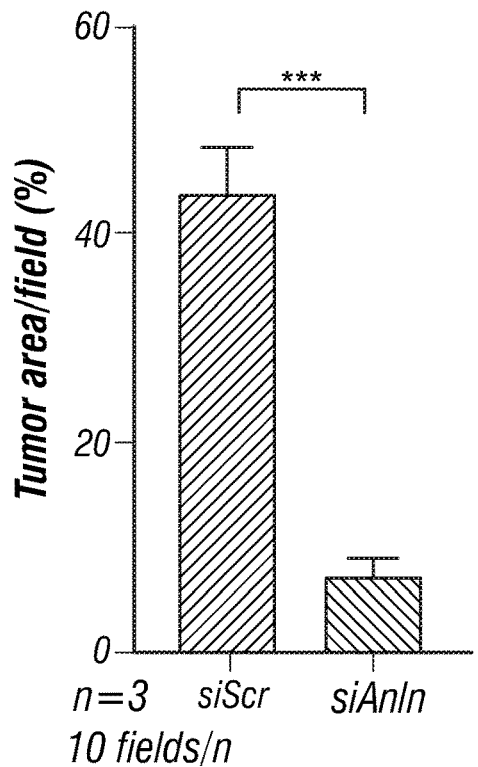
Figure 4J:
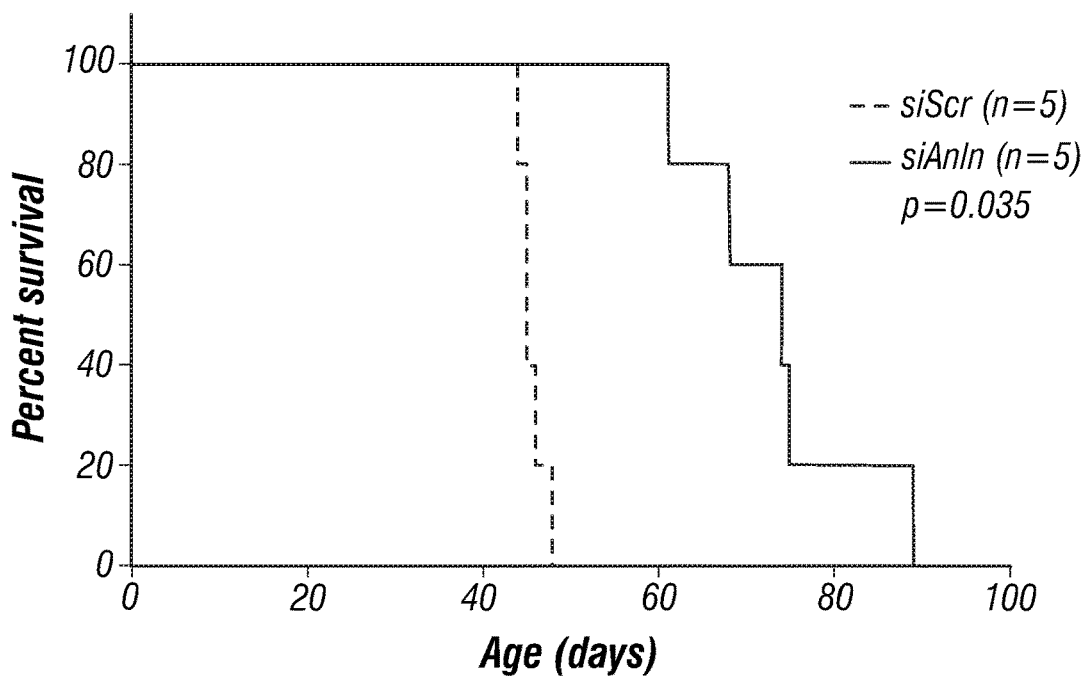

Anln expression is required for MYC-driven liver cancer formation in transgenic mouse model. To investigate whether targeting Anln affects liver tumorigenesis in an endogenous liver cancer model, the inventors examined its role in the well-established LAP-tTa; TRE-MYC liver cancer mouse model (Shachaf et al., 2012) (FIG. 4A), in which human c-MYC can be temporally activated specifically in liver by simply withdrawing Dox water at the time of birth (FIG. 4B). This model has complete penetrance and yields robust and aggressive liver cancer with median survival around 50 days old. To suppress Anln expression in this mouse model, the inventors delivered Anln siRNA (siAnln) vs. scramble siRNA (siScr) via lipid nanoparticles into these mice from p10 to p25, twice a week, 5 times in total (FIG. 4B). At p34, they collected a few mice to assess their tumor burden. The inventors found that while there was no difference in their liver to body weight ratios (FIG. 4F), the siAnln treated group had significantly fewer liver tumor nodules than the siScr group as evident by the gross appearance of the livers and their histology (FIGS. 4G-I). Moreover, the survival of the siAnln treated group was significantly improved compared to that of the siScr group (FIG. 4J; p=0.035). These results suggested that elevated Anln expression and normal cytokinesis are required for efficient transformation of MYC-induced HCC.

Figure 5B:
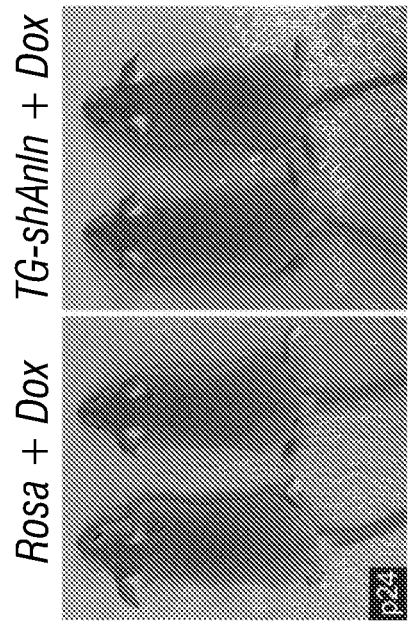
FIGS. 5A-H: An inducible transgenic mouse model to inhibit Anln expression and cytokinesis.
Figure 5D:
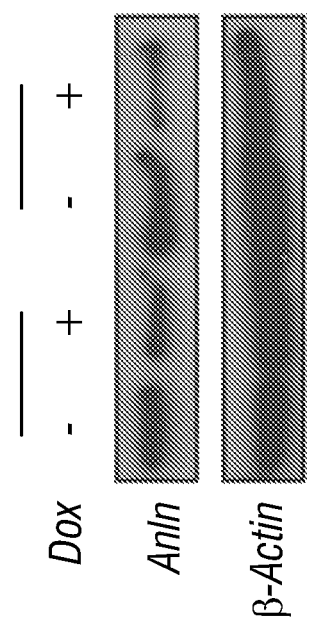
Figure 5A:
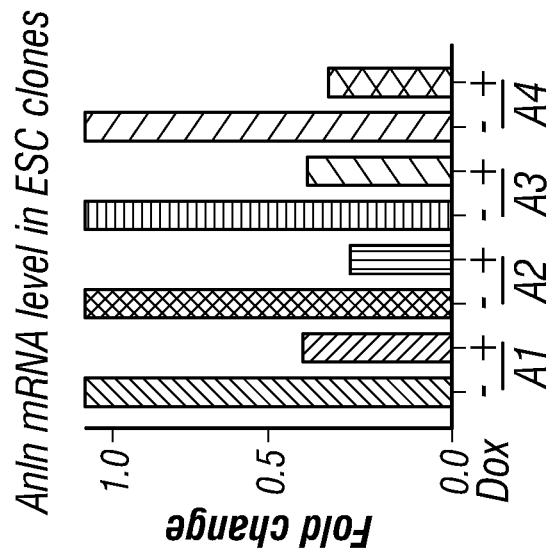
Figure 5C:
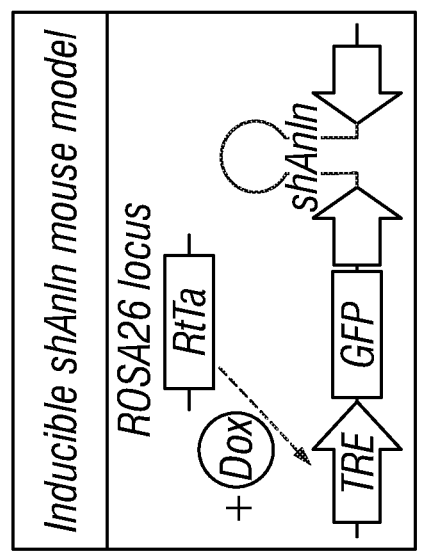
Figure 5G:
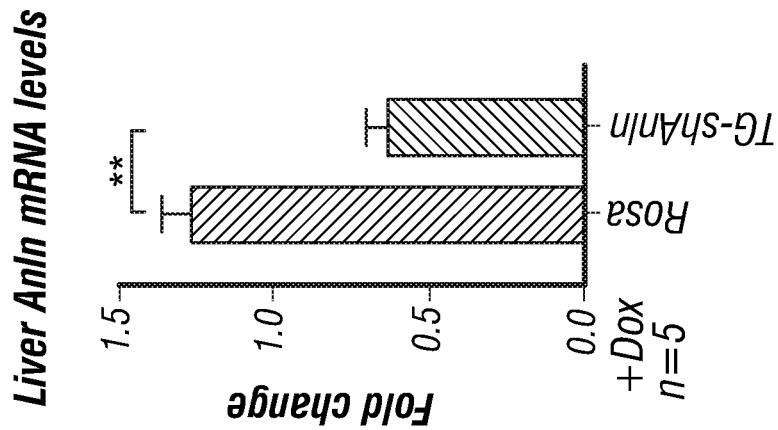
Figure 5F:
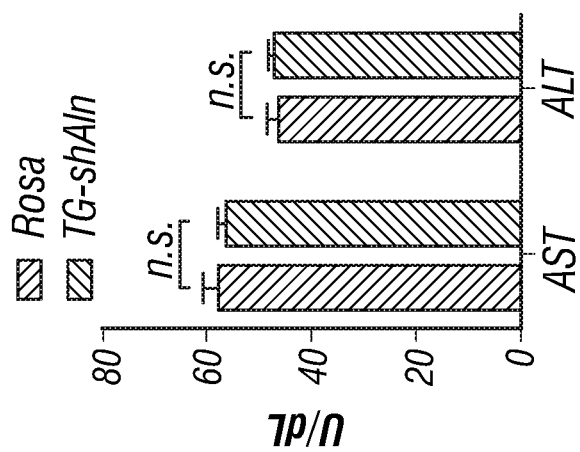
Figure 5E:
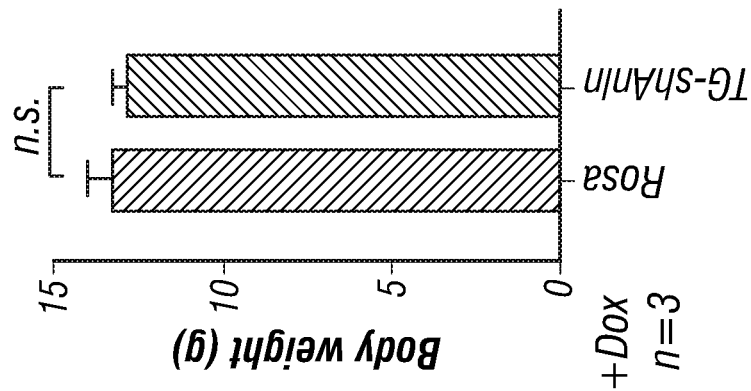
Figure 5H:
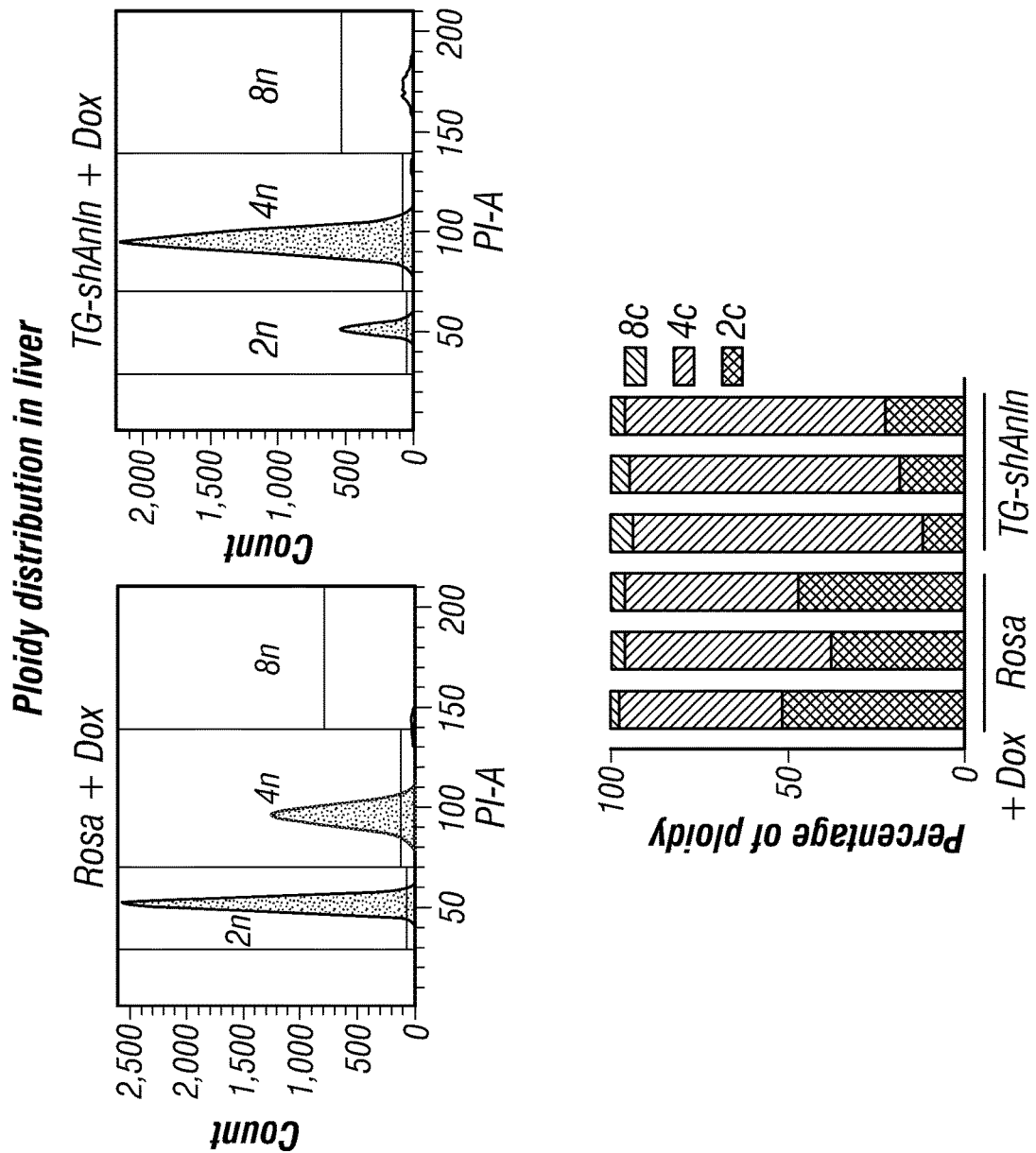

Inducible shAnln transgenic mice suppressed liver tumorigenesis in DEN plus CCL4 cancer model Next, the inventors wanted to generate a more potent mouse model to inhibit Anln expression. Thus, they created a doxycycline (dox)-inducible transgenic mouse expressing an shRNA against Anln. Transgenic mice were derived from embryonic stem cells containing Rosa-rtTA and a GFP+shAnln cassette under the control of a tetracycline responsive promoter element (TRE) (FIGS. 5B-C; transgenic design based on Premsrirut et al., 2011). Dox could be used to induce Anln suppression in a temporally specific fashion (FIG. 5A). Rosa-rtTa alone or Rosa-rtTa; TRE-shAnln (hereafter called Rosa and TG-shAnln) transgenic mice exposed to dox water from P0-P20 showed normal growth, development, and liver function (FIG. 5D-F). Anln mRNA levels were suppressed by 50% (FIG. 5G), which resulted in hyperpolyploid livers after dox withdrawal (FIG. 6H), demonstrating the successful inhibition of cytokinesis.

Figure 6A:
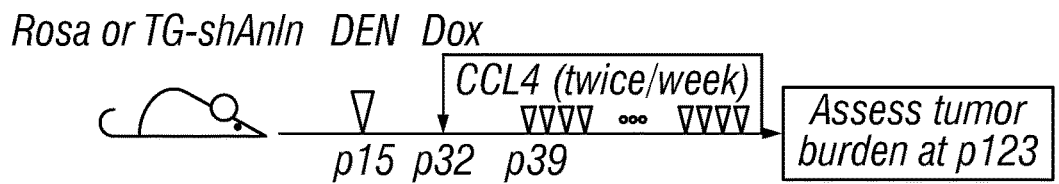
FIGS. 6A-C: Inducible shAnln transgenic mouse shows protection against DEN plus CCL4 induced HCCs.
Figure 6B:
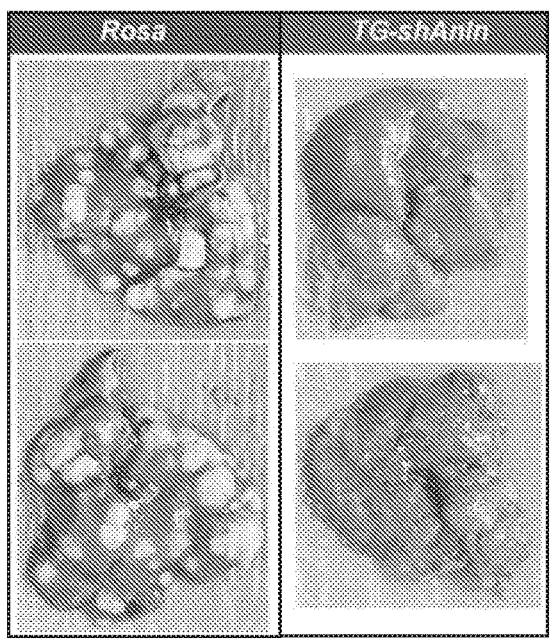
Figure 6C:
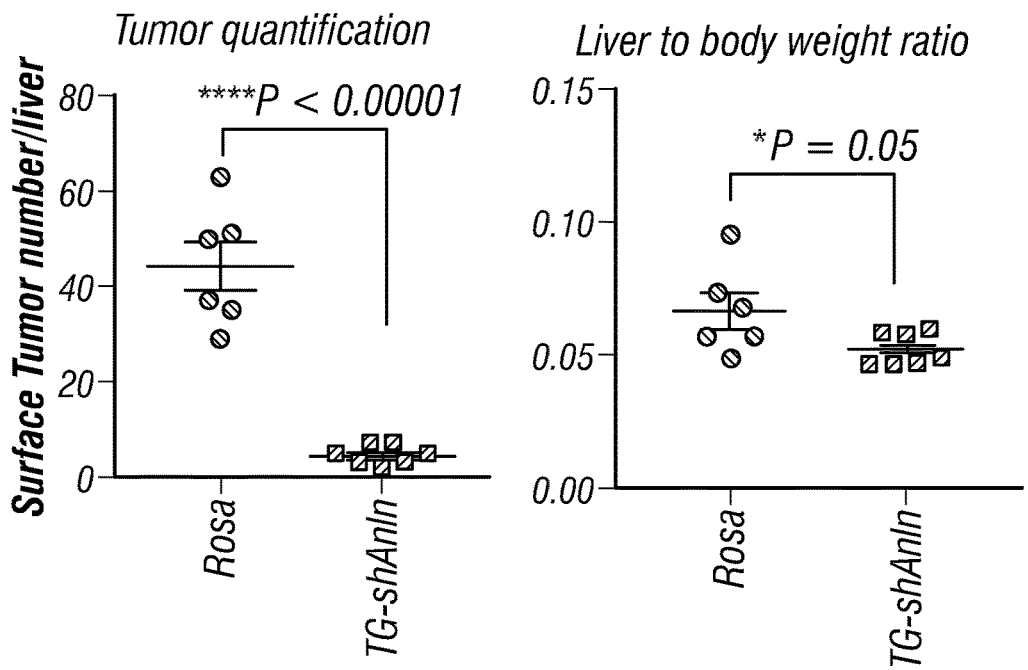

To test whether inhibiting Anln can lead to suppressed tumorigenesis in a mouse cancer model that is more reflective of human disease states, the inventors gave these mice a single dose intraperitoneal (IP) dose (25 µg/g) of the agent diethylnitrosamine (DEN) to both cohorts at p15 to induce HCC. At the age of p32, they fed both Rosa and TG-shAnln mice with Dox water (1 g/L) to induce shAnln, and then started Carbon Tetracloride (CCL4) injury a week later (p39), two times a week (FIG. 6A). After 12 weeks of CCL4 injury, they assessed the tumor burden in these mice and found that the TG-shAnln mice exhibited significantly reduced gross tumor burden (FIGS. 6B-C). These results confirmed that inhibiting cytokinesis via knocking down Anln suppressed HCC formation in multiple liver cancer models.

Figure 7A:
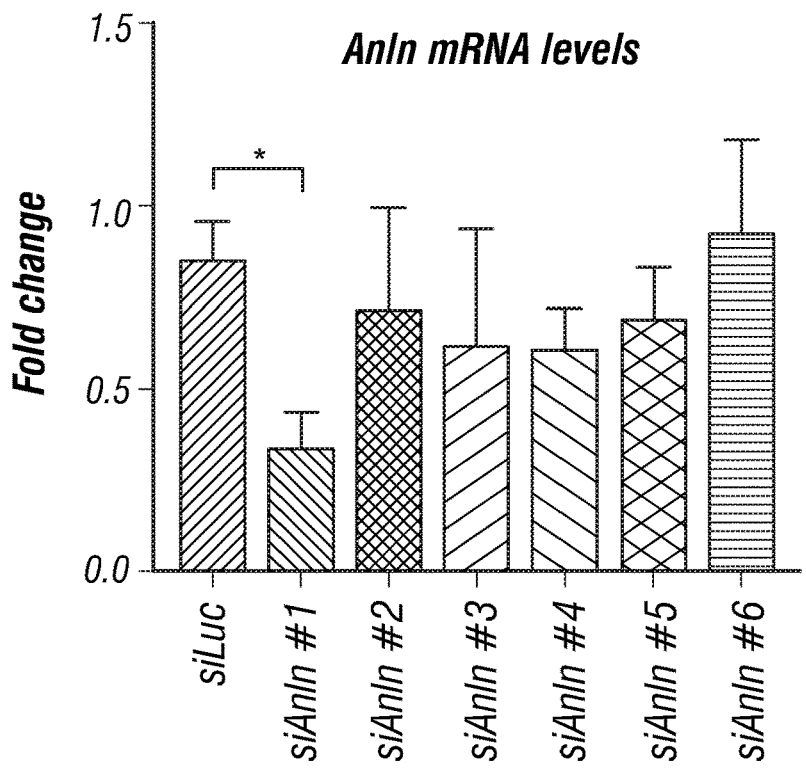
FIGS. 7A-E: Suppression of Anln has unnoticeable impact on tissue homeostasis and regenerative capacity of the liver.
Figure 7B:
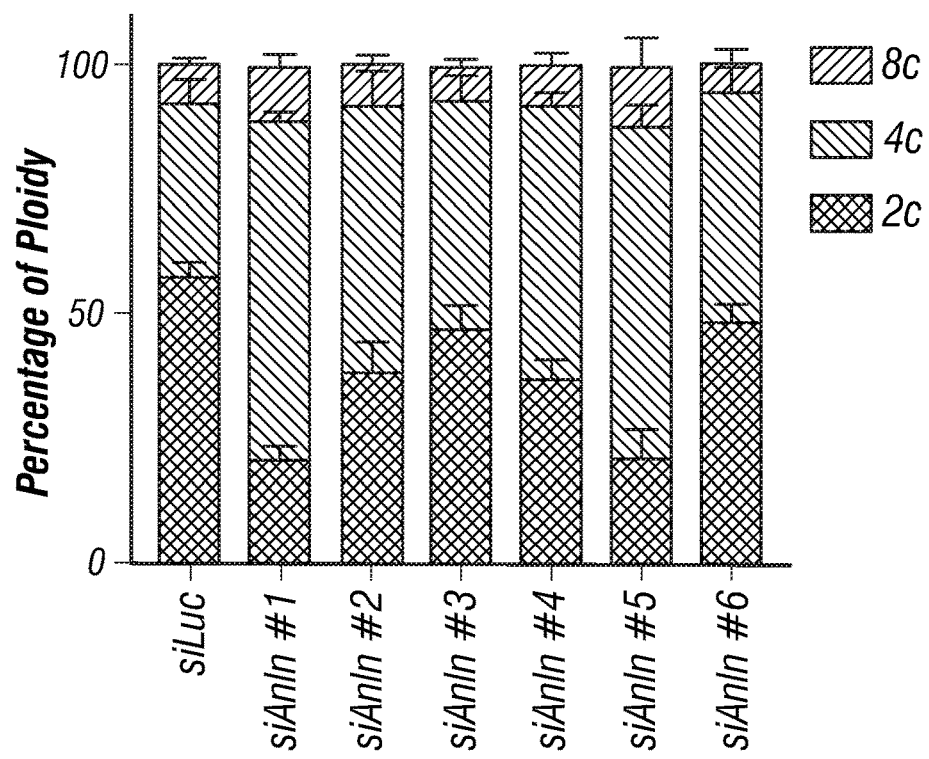

In vivo knockdown of Anln did not interfere with liver function or regeneration. While inducing cytokinesis failure through knocking down Anln can be beneficial in combating against cancer cells, the inventors needed to assess whether this approach causes any harm to the surrounding normal liver cells if they were to use it against cancer cells in vivo. To this end, the inventors collaborated with Anylam pharmaceutical company and obtained from them 6 different top-of-the-line GalNAc-conjugated siRNAs against Anln and 1 control siRNA against firefly luciferase (siLuc). They subcutaneously injected each of these GalNAc-siRNA into WT mice at 1.0 mg/kg (once every week, two times in total) and collected their liver tissues 3 days later to assess the knockdown efficiency and polyploidization (FIGS. 7A-B). Based on the results of this experiment, the inventors selected siRNA #1 (it will be referred to as shAnln from here onward) for subsequent in vivo experiments.

Figure 7C:
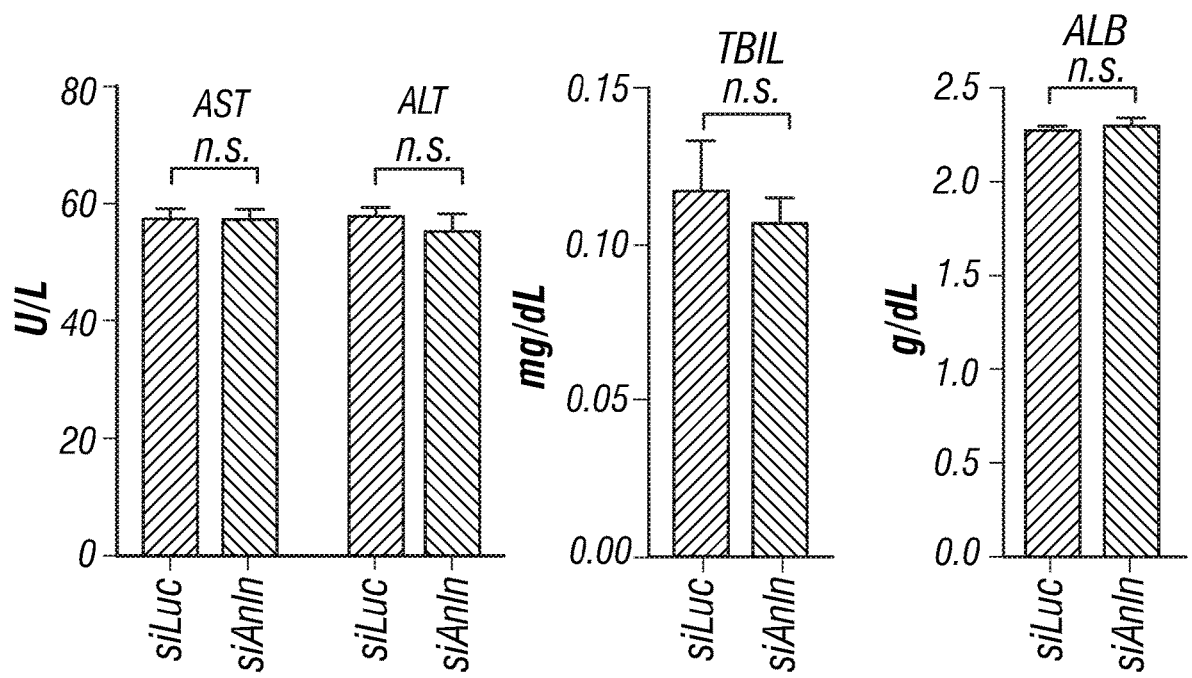
Figure 7D:
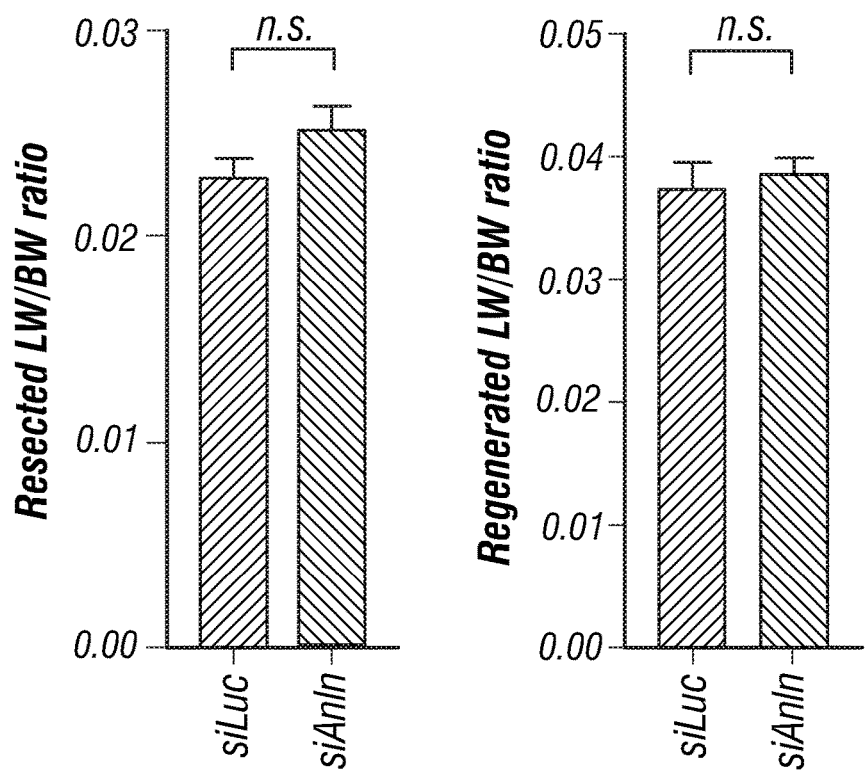
Figure 7E:
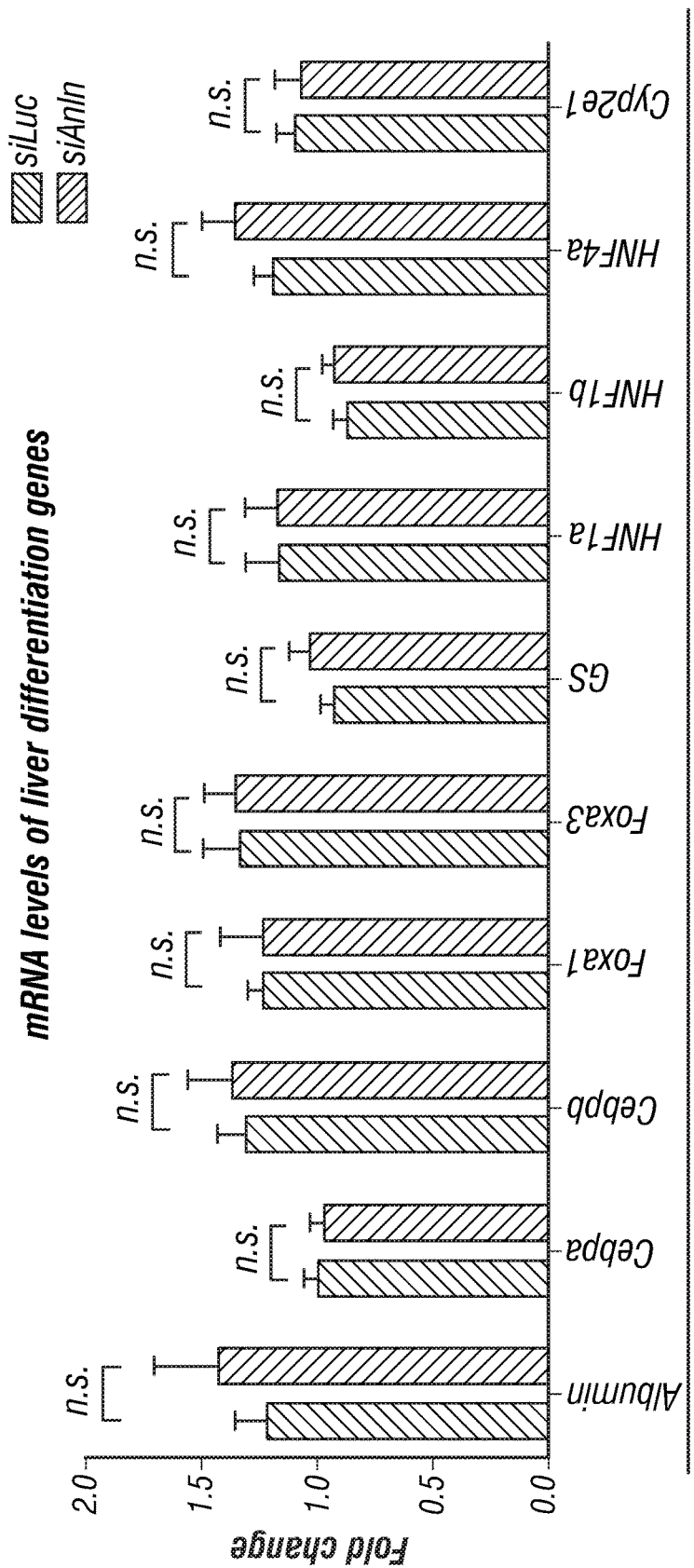

After 2 doses of either siAnln or siLuc at 1.0 mg/kg 4 days apart from each other, the inventors collected blood serum for liver function tests and found that all the measured variables from both groups, such as AST, ALT, TBIL, and ALB were not noticeably different from normal level nor from each other (FIG. 7C), suggesting that suppressing Anln using siAnln did not lead to significant cellular damage.

Although suppression of Anln by siAnln did not cause damage to the liver and change its cellular differentiation, it could potentially inhibit normal cell growth and regeneration. To investigate whether suppression of Anln compromises the ability of the liver to regenerate after injury, the inventors performed partial hepatectomy, a surgical procedure in which ⅔ of the liver is removed, on both siLuc and siAnln treated groups of mice. Surprisingly, they saw siAnln treated mice were able to regenerate their liver as well as siLuc treated mice, based on the similarity in their regenerated liver weight to body weight (LW/BW) ratios. Together, these data demonstrated that suppression of Anln has unnoticeable impact on tissue homeostasis and regenerative capacity of the liver.

All of the methods disclosed and claimed herein can be made and executed without undue experimentation in light of the present disclosure. While the compositions and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims

VII. REFERENCES

The following references, to the extent that they provide exemplary procedural or other details supplementary to those set forth herein, are specifically incorporated herein by reference.

Br. Patent No. 1,529,202
EP 266,032
PCT Appln. WO 00/44914
PCT Appln. WO 01/68836
PCT Appln. WO 99/32619
U.S. Pat. No. 3,832,253
U.S. Pat. No. 3,854,480
U.S. Pat. No. 4,337,063
U.S. Pat. No. 4,404,289
U.S. Pat. No. 4,405,711
U.S. Pat. No. 4,415,723
U.S. Pat. No. 4,452,775
U.S. Pat. No. 4,458,066
U.S. Pat. No. 4,659,774
U.S. Pat. No. 4,667,013
U.S. Pat. No. 4,675,189
U.S. Pat. No. 4,682,195
U.S. Pat. No. 4,683,202
U.S. Pat. No. 4,704,362
U.S. Pat. No. 4,748,034
U.S. Pat. No. 4,816,571
U.S. Pat. No. 4,959,463
U.S. Pat. No. 5,133,974
U.S. Pat. No. 5,141,813
U.S. Pat. No. 5,214,136
U.S. Pat. No. 5,221,619
U.S. Pat. No. 5,223,618
U.S. Pat. No. 5,239,660
U.S. Pat. No. 5,264,566
U.S. Pat. No. 5,268,486
U.S. Pat. No. 5,378,825
U.S. Pat. No. 5,407,686
U.S. Pat. No. 5,428,148
U.S. Pat. No. 5,446,137
U.S. Pat. No. 5,466,786
U.S. Pat. No. 5,470,967
U.S. Pat. No. 5,480,980
U.S. Pat. No. 5,554,744
U.S. Pat. No. 5,574,146
U.S. Pat. No. 5,583,013
U.S. Pat. No. 5,602,240
U.S. Pat. No. 5,602,240
U.S. Pat. No. 5,602,244
U.S. Pat. No. 5,610,289
U.S. Pat. No. 5,614,617
U.S. Pat. No. 5,623,070
U.S. Pat. No. 5,637,683
U.S. Pat. No. 5,645,897
U.S. Pat. No. 5,652,099

U.S. Pat. No. 5,670,663
U.S. Pat. No. 5,672,697
U.S. Pat. No. 5,672,697
U.S. Pat. No. 5,681,947
U.S. Pat. No. 5,700,922
U.S. Pat. No. 5,705,629
U.S. Pat. No. 5,708,154
U.S. Pat. No. 5,714,606
U.S. Pat. No. 5,728,525
U.S. Pat. No. 5,736,152
U.S. Pat. No. 5,739,169
U.S. Pat. No. 5,763,167
U.S. Pat. No. 5,777,092
U.S. Pat. No. 5,792,847
U.S. Pat. No. 5,795,715
U.S. Pat. No. 5,801,005
U.S. Pat. No. 5,824,311
U.S. Pat. No. 5,830,880
U.S. Pat. No. 5,846,945
U.S. Pat. No. 5,858,988
U.S. Pat. No. 5,859,221
U.S. Pat. No. 5,872,232
U.S. Pat. No. 5,886,165
U.S. Pat. No. 5,889,136
U.S. Pat. No. 5,889,136
U.S. Pat. No. 6,251,666
*Animal Cell Culture* (Freshney, Ed., 1987)
Austin-Ward and Villaseca, *Rev. Med. Chil.*, 126(7):838-45, 1998.
Bosher and Labouesse, *Nat. Cell. Biol.*, 2:E31-E36, 2000.
Bukowski et al., *Clin. Cancer Res.*, 4(10):2337-47, 1998.
Caplen et al., *Gene*, 252(1-2):95-105, 2000.
Christodoulides et al., *Microbiology*, 144(Pt 11):3027-3037, 1998.
Davidson et al., *J. Immunother.*, 21(5):389-98, 1998.
Davis, L. et al., Basic Methods in Molecular Biology, 1986.
Elbashir et al., *Nature*, 411(6836):494-498, 2001.
Fire et al., *Nature*, 391:806-811, 1998.
Froehler et al., Nucleic Acids Res., 14(13):5399-5407, 1986.
Gillam et al., *J. Biol. Chem.*, 253(8):2532-2539, 1978.
Giovanella et al., J. Natl. Can. Inst., 52: 921-30, 1974.
Grishok et al., *Science*, 287:2494-2497, 2000.
Hanibuchi et al., *Int. J. Cancer*, 78(4):480-485, 1998.
Hellstrand et al., *Acta Oncol.*, 37(4):347-353, 1998.
Hui and Hashimoto, *Infection Immun.*, 66(11):5329-5336, 1998.
Itakura et al., *J. Am. Chem. Soc.*, 97(25):7327-7332, 1975.
Ketting et al., *Cell*, 99:133-141, 1999.
Kornberg and Baker, In: *DNA Replication*, 2d Ed., Freeman, San Francisco, 1992.
Li et al., Clin. Exp. Metastasis, 17:423-9, 1999.
Lin and Avery, *Nature*, 402:128-129, 1999.
Mitchell et al., *Ann. NY Acad Sci.*, 690:153-166, 1993.
Montgomery et al., *Proc. Natl. Acad. Sci. USA*, 95:155-2-15507, 1998.
Morton et al., *Arch. Surg.*, 127:392-399, 1992.
Pietras et al., *Oncogene*, 17(17):2235-49, 1998.

Pilkington et al., Anticancer Res., 17: 4107-9, 1997.
Qin et al., *Proc. Natl. Acad. Sci. USA,* 95(24):14411-14416, 1998.
Ravindranath and Morton, *Intern. Rev. Immunol.*, 7: 303-329, 1991.
Ribatta et al., Intl. JS. Dev. Biol., 40: 1189-97, 1999.
Rosenberg et al., *Ann. Surg.* 210(4):474-548, 1989.
Rosenberg et al., *N. Engl. J. Med.*, 319:1676, 1988.
Sambrook et al., In: *Molecular cloning*, Cold Spring Harbor Laboratory Press, Cold Spring Harbor, N.Y., 1989, 1990, 2001 and 2003.
Schneider et al., Tetrahedron Lett. 31:335 and references cited therein, 1990.
Sharp and Zamore, *Science*, 287:2431-2433, 2000.
Sharp, *Genes Dev.*,13:139-141, 1999.
Tabara et al., *Cell*, 99:123-132, 1999.
Uhlmann et al., Chem. Rev. 90:543-584, 1990.
Wincott et al., *Nucleic Acids Res.*, 23(14):2677-2684, 1995.
Barr, F. A. and U. Gruneberg, *Cell*, 2007. 131(5): p. 847-60.
Fujiwara et al., *Nature*, 2005. 437(7061): p. 1043-7.
Pampalona et al., *PLoS Genet*, 2012. 8(4): p. e1002679.
Lv et al., *Cell Cycle*, 2012. 11(15): p. 2864-75.
Hognas et al., *Oncogene*, 2012. 31(31): p. 3597-3606.
Niu et al., *Oncogene*, April 24. doi: 10.1038/onc.2017.72 (epub ahead of print).
Mittal et al., *Br J Cancer,* 2017. 116(9): p. 1186-1194.
Davoli et al., *Science*, 2017. 355(6322).
Duncan, A. W., *Semin Cell Dev Biol*, 2013. 24(4): p. 347-56.
Duncan et al., *Gastroenterology*, 2012. 142(1): p. 25-28.
Duncan et al., *Nature*, 2010. 467(7316): p. 707-U93.
Gentric et al., *Int J Hepatol*, 2012. 2012: p. 282430.
Celton-Morizur et al., *J Clinical Investigation*, 2009. 119(7): p. 1880-1887.
Margall-Ducos et al., *J Cell Science*, 2007. 120(20): p. 3633-3639.
Simson, I. W., *J Pathol Bacteriol*, 1963. 85: p. 35-9.
Duncan et al., *Gastroenterology*, 2012. 142(1): p. 25-8.
Hickson, G. R. and P. H. O'Farrell, *Biochem Soc Trans*, 2008. 36(Pt 3): p. 439-41.
Piekny, A. J. and A. S. Maddox, *Semin Cell Dev Biol*, 2010. 21(9): p. 881-91.
D'Avino et al., *Methods Mol Biol*, 2009. 545: p. 99-112.
Oegema et al., *J Cell Biol*, 2000. 150(3): p. 539-52.
Field, C. M. and B. M. Alberts, *J Cell Biol*, 1995. 131(1): p. 165-78.
Giansanti et al., *J Cell Science*, 1999. 112(14): p. 2323-2334.
Oegema et al., *J Cell Biology*, 2000. 150(3): p. 539-551.
Hall et al., *Clin Cancer Res*, 2005. 11(19 Pt 1): p. 6780-6.
Wang et al., *Cancer Biomark*, 2016. 16(3): p. 459-65.
Zhou et al., *Mol Cell Biochem*, 2015. 398(1-2): p. 11-9.
Zuber et al., *Nature Biotechnology*, 2011. 29(1): p. 79-+.
Azuma et al., *Nature Biotechnology,* 2007. 25(8): p. 903-910.
Shafritz, D. A., *Nature Biotechnology,* 2007. 25(8): p. 871-2.
Grompe, M. and S. Strom, *Gastroenterology*, 2013. 145(6): p. 1209-14.
Shachaf et al., *Nature*, 2004. 431(2012): p. 1112-7.
Premsrirut et al., *Cell*, 2011. 145(1): p. 145-58.

What is claimed is:

1. A method of treating a liver cancer in a subject comprising administering to the subject an effective amount of an interfering RNA or vector encoding the interfering RNA, where the interfering RNA targets an anillin actin binding protein mRNA.

2. The method of claim 1, wherein the interfering RNA or vector is delivered by liposome or nanoparticle.

3. The method of claim 1, wherein said interfering RNA or vector is administered systemically or regional to said liver cancer.

4. The method of claim 1, wherein said interfering RNA or vector is administered intravenously, intratumorally, intrahepatically, intra-arterially, subcutaneously, topically or orally.

5. The method of claim 1, wherein the method further comprises administering an additional anti-cancer therapy to the individual.

6. The method of claim 5, wherein the additional anti-cancer therapy comprises surgery, radiation, chemotherapy, hormone therapy, immunotherapy, or a combination thereof.

7. The method of claim 6, wherein the radiation comprises external beam radiation therapy.

8. The method of claim 1, wherein said administering is repeated.

9. The method of claim 1, wherein said liver cancer is recurrent or drug resistant.

10. The method of claim 1, wherein said interfering RNA is about 21-23 bases in length.

11. The method of claim 1, comprising a sequence at least 80%, 85%, 90% or 95% identical to SEQ ID NO: 1.

12. The method of claim 1, comprising the sequence of SEQ ID NO: 1.

13. The method of claim 1, consisting of the sequence of SEQ ID NO: 1.

14. The method of claim 1, wherein the liver cancer is metastatic from a liver cancer or metastatic to the liver.

* * * * *

SEQUENCE LISTING

<160> NUMBER OF SEQ ID NOS: 3

<210> SEQ ID NO 1
<211> LENGTH: 21
<212> TYPE: DNA

<213> ORGANISM: Artificial sequence
<220> FEATURE:
<223> OTHER INFORMATION: Synthetic oligonucleotide

<400> SEQUENCE: 1

```
ggcucucugc agauacuaat t                                              21
```

<210> SEQ ID NO 2
<211> LENGTH: 4804
<212> TYPE: DNA
<213> ORGANISM: Homo sapiens

<400> SEQUENCE: 2

```
cccagcgcgc atgctcgcgg ctcggcgctg aaattcaaat ttgaacggct gcagaggccg      60
agtccgtcac tggaagccga gaggagagga cagctggttg tgggagagtt ccccccgcctc    120
agactcctgg ttttttccag gagacacact gagctgagac tcactttttct cttcctgaat    180
ttgaaccacc gtttccatcg tctcgtagtc cgacgcctgg ggcgatggat ccgtttacgg     240
agaaactgct ggagcgaacc cgtgccaggc gagagaatct tcagagaaaa atggctgaga     300
ggcccacagc agctccaagg tctatgactc atgctaagcg agctagacag ccactttcag     360
aagcaagtaa ccagcagccc ctctctggtg gtgaagagaa atcttgtaca aaaccatcgc     420
catcaaaaaa acgctgttct gacaacactg aagtagaagt ttctaacttg gaaaataaac     480
aaccagttga gtcgacatct gcaaaatctt gttctccaag tcctgtgtct cctcaggtgc     540
agccacaagc agcagatacc atcagtgatt ctgttgctgt cccggcatca ctgctgggca     600
tgaggagagg gctgaactca agattggaag caactgcagc ctcctcagtt aaaacacgta     660
tgcaaaaact gcagagcaa cggcgccgtt gggataatga tgatatgaca gatgacattc      720
ctgaaagctc actcttctca ccaatgccat cagaggaaaa ggctgcttcc cctcccagac     780
ctctgctttc aaatgcctcg gcaactccag ttggcagaag gggccgtctg gccaatcttg     840
ctgcaactat ttgctcctgg gaagatgatg taaatcactc atttgcaaaa caaacagtg      900
tacaagaaca gcctggtacc gcttgtttat ccaaattttc ctctgcaagt ggagcatctg     960
ctaggatcaa tagcagcagt gttaagcagg aagctacatt ctgttcccaa agggatggcg    1020
atgcctcttt gaataaagcc ctatcctcaa gtgctgatga tgcgtctttg gttaatgcct    1080
caatttccag ctctgtgaaa gctacttctc cagtgaaatc tactacatct atcactgatg    1140
ctaaaagttg tgagggacaa atcctgagc tacttccaaa aactcctatt agtcctctga     1200
aaacgggggt atcgaaacca attgtgaagt caactttatc ccagacagtt ccatccaagg    1260
gagaattaag tagagaaatt tgtctgcaat ctcaatctaa agacaaatct acgacaccag    1320
gaggaacagg aattaagcct tcctggaac gctttggaga gcgttgtcaa gaacatagca    1380
aagaaagtcc agctcgtagc acccccaca gaaccccccat tattactcca aatacaaagg    1440
ccatccaaga aagattattc aagcaagaca catcttcatc tactacccat ttagcacaac    1500
agctcaagca ggaacgtcaa aaagaactag catgtcttcg tggccgattt gacaagggca    1560
atatatggag tgcagaaaaa ggcggaaact caaaaagcaa acaactagaa accaaacagg    1620
aaactcactg tcagagcact cccctcaaaa acaccaagg tgtttcaaaa actcagtcac     1680
ttccagtaac agaaaaggtg accgaaaacc agataccagc caaaaattct agtacagaac    1740
ctaaaggttt cactgaatgc gaaatgacga atctagccc tttgaaaata acattgtttt    1800
tagaagagga caaatcctta aaagtaacat cagacccaaa ggttgagcag aaaattgaag    1860
tgatacgtga aattgagatg agtgtggatg atgatgatat caatagttcg aaagtaatta    1920
```

```
atgacctctt cagtgatgtc ctagaggaag gtgaactaga tatggagaag agccaagagg   1980
agatggatca agcattagca gaaagcagcg aagaacagga gatgcactg aatatctcct    2040 caatgtcttt acttgcacca ttggcacaaa cagttggtgt ggtaagtcca gagagtttag   2100
tgtccacacc tagactggaa ttgaaagaca ccagcagaag tgatgaaagt ccaaaaccag   2160
gaaaattcca agaactcgt gtccctcgag ctgaatctgg tgatagcctt ggttctgaag    2220
atcgtgatct tctttacagc attgatgcat atagatctca aagattcaaa gaacagaac    2280 gtccatcaat aaagcaggtg attgttcgga aggaagatgt tacttcaaaa ctggatgaaa   2340
aaaataatgc ctttccttgt caagttaata tcaaacagaa aatgcaggaa ctcaataacg    2400
aaataaatat gcaacagaca gtgatctatc aagctagcca ggctcttaac tgctgtgttg    2460
atgaagaaca tggaaaaggg tccctagaag aagctgaagc agaaagactt cttctaattg    2520
caactgggaa gagaacactt ttgattgatg aattgaataa attgaagaac gaaggacctc    2580
agaggaagaa taaggctagt ccccaaagtg aatttatgcc atccaaagga tcagttactt    2640
tgtcagaaat ccgcttgcct ctaaaagcag attttgtctg cagtacggtt cagaaaccag    2700
atgcagcaaa ttactattac ttaattatac taaaagcagg agctgaaaat atggtagcca    2760
caccattagc aagtacttca aactctctta cggtgatgc tctgacattc actactacat     2820
ttactctgca agatgtatcc aatgactttg aaataaatat tgaagtttac agcttggtgc    2880
aaaagaaaga tccctcaggc cttgataaga agaaaaaaac atccaagtcc aaggctatta    2940
ctccaaagcg actcctcaca tctataacca caaaaagcaa cattcattct tcagtcatgg    3000
ccagtccagg aggtcttagt gctgtgcgaa ccagcaactt cgcccttgtt ggatcttaca    3060
cattatcatt gtcttcagta ggaaatacta agtttgttct ggacaaggtc ccctttttat    3120 cttcttttgga aggtcatatt tatttaaaaa taaaatgtca agtgaattcc agtgttgaag   3180
aaagaggttt tctaaccata tttgaagatg ttagtggttt tggtgcctgg catcgaagat    3240
ggtgtgttct ttctggaaac tgtatatctt attggactta tccagatgat gagaaacgca    3300
agaatcccat aggaaggata aatctggcta attgtaccag tcgtcagata gaaccagcca    3360
acagagaatt ttgtgcaaga cgcaacactt ttgaattaat tactgtccga ccacaaagag    3420
aagatgaccg agagactctt gtcagccaat gcagggacac actctgtgtt accaagaact    3480
ggctgtctgc agatactaaa gaagagcggg atctctggat gcaaaaactc aatcaagttc    3540
ttgttgatat tcgcctctgg caacctgatg cttgctacaa acctattgga aagccttaaa    3600
ccgggaaatt tccatgctat ctagaggttt ttgatgtcat cttaagaaac acacttaaga    3660
gcatcagatt tactgattgc attttatgct ttaagtacga aagggtttgt gccaatattc    3720
actacgtatt atgcagtatt tatatctttt gtatgtaaaa ctttaactga tttctgtcat    3780
tcatcaatga gtagaagtaa atacattata gttgattttg ctaaatctta atttaaaagc    3840 ctcatttttcc tagaaatcta attattcagt tattcatgac aatatttttt taaaagtaag    3900
aaattctgag ttgtcttctt ggagctgtag gtcttgaagc agcaacgtct tcaggggtt     3960 ggagacagaa acccattctc caatctcagt agttttttcg aaaggctgtg atcatttatt    4020
gatcgtgata tgacttgtta ctagggtact gaaaaaaatg tctaaggcct ttacagaaac    4080
atttttagta atgaggatga gaacttttc aaatagcaaa tatatattgg cttaaagcat     4140
gaggctgtct tcagaaaagt gatgtggaca taggaggcaa tgtgtgagac ttggggggttc    4200 aatatttttat atagaagagt taataagcac atggtttaca tttactcagc tactatatat   4260
```

-continued

```
gcagtgtggt gcacattttc acagaattct ggcttcatta agatcattat ttttgctgcg    4320
tagcttacag acttagcata ttagttttt ctactcctac aagtgtaaat tgaaaaatct    4380
ttatattaaa aaagtaaact gttatgaagc tgctatgtac taataatact ttgcttgcca    4440
aagtgtttgg gttttgttgt tgtttgtttg tttgtttgtt tttggttcat gaacaacagt    4500
gtctagaaac ccattttgaa agtggaaaat tattaagtca cctatcacct ttaaacgcct    4560
ttttttaaaa ttataaaata ttgtaaagca gggtctcaac ttttaaatac actttgaact    4620
tcttctctga attattaaag ttctttatga cctcatttat aaacactaaa ttctgtcacc    4680
tcctgtcatt ttatttttta ttcattcaaa tgtatttttt cttgtgcata ttataaaaat    4740
atattttatg agctcttact caaataaata cctgtaaatg tctaaaggaa aaaaaaaaa     4800 aaaa                                                                 4804
```

<210> SEQ ID NO 3
<211> LENGTH: 1124
<212> TYPE: PRT
<213> ORGANISM: Homo sapiens

<400> SEQUENCE: 3

```
Met Asp Pro Phe Thr Glu Lys Leu Leu Glu Arg Thr Arg Ala Arg Arg
1               5                   10                  15

Glu Asn Leu Gln Arg Lys Met Ala Glu Arg Pro Thr Ala Ala Pro Arg
            20                  25                  30

Ser Met Thr His Ala Lys Arg Ala Arg Gln Pro Leu Ser Glu Ala Ser
        35                  40                  45

Asn Gln Gln Pro Leu Ser Gly Gly Glu Lys Ser Cys Thr Lys Pro
    50                  55                  60

Ser Pro Ser Lys Lys Arg Cys Ser Asp Asn Thr Glu Val Glu Val Ser
65                  70                  75                  80

Asn Leu Glu Asn Lys Gln Pro Val Glu Ser Thr Ser Ala Lys Ser Cys
                85                  90                  95

Ser Pro Ser Pro Val Ser Pro Gln Val Gln Pro Gln Ala Ala Asp Thr
            100                 105                 110

Ile Ser Asp Ser Val Ala Val Pro Ala Ser Leu Leu Gly Met Arg Arg
        115                 120                 125

Gly Leu Asn Ser Arg Leu Glu Ala Thr Ala Ala Ser Ser Val Lys Thr
    130                 135                 140

Arg Met Gln Lys Leu Ala Glu Gln Arg Arg Trp Asp Asn Asp Asp
145                 150                 155                 160

Met Thr Asp Asp Ile Pro Glu Ser Ser Leu Phe Ser Pro Met Pro Ser
                165                 170                 175

Glu Glu Lys Ala Ala Ser Pro Pro Arg Pro Leu Leu Ser Asn Ala Ser
            180                 185                 190

Ala Thr Pro Val Gly Arg Arg Gly Arg Leu Ala Asn Leu Ala Ala Thr
        195                 200                 205

Ile Cys Ser Trp Glu Asp Asp Val Asn His Ser Phe Ala Lys Gln Asn
    210                 215                 220

Ser Val Gln Glu Gln Pro Gly Thr Ala Cys Leu Ser Lys Phe Ser Ser
225                 230                 235                 240

Ala Ser Gly Ala Ser Ala Arg Ile Asn Ser Ser Val Lys Gln Glu
                245                 250                 255

Ala Thr Phe Cys Ser Gln Arg Asp Gly Asp Ala Ser Leu Asn Lys Ala
            260                 265                 270
```

```
Leu Ser Ser Ser Ala Asp Asp Ala Ser Leu Val Asn Ala Ser Ile Ser
            275                 280                 285
Ser Ser Val Lys Ala Thr Ser Pro Val Lys Ser Thr Thr Ser Ile Thr
        290                 295                 300
Asp Ala Lys Ser Cys Glu Gly Gln Asn Pro Glu Leu Leu Pro Lys Thr
305                 310                 315                 320
Pro Ile Ser Pro Leu Lys Thr Gly Val Ser Lys Pro Ile Val Lys Ser
                325                 330                 335
Thr Leu Ser Gln Thr Val Pro Ser Lys Gly Glu Leu Ser Arg Glu Ile
            340                 345                 350
Cys Leu Gln Ser Gln Ser Lys Asp Lys Ser Thr Thr Pro Gly Gly Thr
        355                 360                 365
Gly Ile Lys Pro Phe Leu Glu Arg Phe Gly Glu Arg Cys Gln Glu His
    370                 375                 380
Ser Lys Glu Ser Pro Ala Arg Ser Thr Pro His Arg Thr Pro Ile Ile
385                 390                 395                 400
Thr Pro Asn Thr Lys Ala Ile Gln Glu Arg Leu Phe Lys Gln Asp Thr
                405                 410                 415
Ser Ser Ser Thr Thr His Leu Ala Gln Gln Leu Lys Gln Glu Arg Gln
            420                 425                 430
Lys Glu Leu Ala Cys Leu Arg Gly Arg Phe Asp Lys Gly Asn Ile Trp
        435                 440                 445
Ser Ala Glu Lys Gly Gly Asn Ser Lys Ser Lys Gln Leu Glu Thr Lys
    450                 455                 460
Gln Glu Thr His Cys Gln Ser Thr Pro Leu Lys Lys His Gln Gly Val
465                 470                 475                 480
Ser Lys Thr Gln Ser Leu Pro Val Thr Glu Lys Val Thr Glu Asn Gln
                485                 490                 495
Ile Pro Ala Lys Asn Ser Ser Thr Glu Pro Lys Gly Phe Thr Glu Cys
            500                 505                 510
Glu Met Thr Lys Ser Ser Pro Leu Lys Ile Thr Leu Phe Leu Glu Glu
        515                 520                 525
Asp Lys Ser Leu Lys Val Thr Ser Asp Pro Lys Val Glu Gln Lys Ile
    530                 535                 540
Glu Val Ile Arg Glu Ile Glu Met Ser Val Asp Asp Asp Ile Asn
545                 550                 555                 560
Ser Ser Lys Val Ile Asn Asp Leu Phe Ser Asp Val Leu Glu Glu Gly
                565                 570                 575
Glu Leu Asp Met Glu Lys Ser Gln Glu Glu Met Asp Gln Ala Leu Ala
            580                 585                 590
Glu Ser Ser Glu Glu Gln Glu Asp Ala Leu Asn Ile Ser Ser Met Ser
        595                 600                 605
Leu Leu Ala Pro Leu Ala Gln Thr Val Gly Val Val Ser Pro Glu Ser
    610                 615                 620
Leu Val Ser Thr Pro Arg Leu Glu Leu Lys Asp Thr Ser Arg Ser Asp
625                 630                 635                 640
Glu Ser Pro Lys Pro Gly Lys Phe Gln Arg Thr Arg Val Pro Arg Ala
                645                 650                 655
Glu Ser Gly Asp Ser Leu Gly Ser Glu Asp Arg Asp Leu Leu Tyr Ser
            660                 665                 670
Ile Asp Ala Tyr Arg Ser Gln Arg Phe Lys Glu Thr Glu Arg Pro Ser
        675                 680                 685
Ile Lys Gln Val Ile Val Arg Lys Glu Asp Val Thr Ser Lys Leu Asp
```

690             695             700
Glu Lys Asn Asn Ala Phe Pro Cys Gln Val Asn Ile Lys Gln Lys Met
705             710             715             720
Gln Glu Leu Asn Asn Glu Ile Asn Met Gln Gln Thr Val Ile Tyr Gln
            725             730             735
Ala Ser Gln Ala Leu Asn Cys Cys Val Asp Glu Glu His Gly Lys Gly
            740             745             750
Ser Leu Glu Glu Ala Glu Ala Glu Arg Leu Leu Leu Ile Ala Thr Gly
            755             760             765
Lys Arg Thr Leu Leu Ile Asp Glu Leu Asn Lys Leu Lys Asn Glu Gly
            770             775             780
Pro Gln Arg Lys Asn Lys Ala Ser Pro Gln Ser Glu Phe Met Pro Ser
785             790             795             800
Lys Gly Ser Val Thr Leu Ser Glu Ile Arg Leu Pro Leu Lys Ala Asp
            805             810             815
Phe Val Cys Ser Thr Val Gln Lys Pro Asp Ala Ala Asn Tyr Tyr Tyr
            820             825             830
Leu Ile Ile Leu Lys Ala Gly Ala Glu Asn Met Val Ala Thr Pro Leu
            835             840             845
Ala Ser Thr Ser Asn Ser Leu Asn Gly Asp Ala Leu Thr Phe Thr Thr
850             855             860
Thr Phe Thr Leu Gln Asp Val Ser Asn Asp Phe Glu Ile Asn Ile Glu
865             870             875             880
Val Tyr Ser Leu Val Gln Lys Lys Asp Pro Ser Gly Leu Asp Lys Lys
            885             890             895
Lys Lys Thr Ser Lys Ser Lys Ala Ile Thr Pro Lys Arg Leu Leu Thr
            900             905             910
Ser Ile Thr Thr Lys Ser Asn Ile His Ser Ser Val Met Ala Ser Pro
            915             920             925
Gly Gly Leu Ser Ala Val Arg Thr Ser Asn Phe Ala Leu Val Gly Ser
            930             935             940
Tyr Thr Leu Ser Leu Ser Ser Val Gly Asn Thr Lys Phe Val Leu Asp
945             950             955             960
Lys Val Pro Phe Leu Ser Ser Leu Glu Gly His Ile Tyr Leu Lys Ile
            965             970             975
Lys Cys Gln Val Asn Ser Ser Val Glu Glu Arg Gly Phe Leu Thr Ile
            980             985             990
Phe Glu Asp Val Ser Gly Phe Gly Ala Trp His Arg Arg Trp Cys Val
            995             1000            1005
Leu Ser Gly Asn Cys Ile Ser Tyr Trp Thr Tyr Pro Asp Asp Glu
1010            1015            1020
Lys Arg Lys Asn Pro Ile Gly Arg Ile Asn Leu Ala Asn Cys Thr
1025            1030            1035
Ser Arg Gln Ile Glu Pro Ala Asn Arg Glu Phe Cys Ala Arg Arg
1040            1045            1050
Asn Thr Phe Glu Leu Ile Thr Val Arg Pro Gln Arg Glu Asp Asp
1055            1060            1065
Arg Glu Thr Leu Val Ser Gln Cys Arg Asp Thr Leu Cys Val Thr
1070            1075            1080
Lys Asn Trp Leu Ser Ala Asp Thr Lys Glu Glu Arg Asp Leu Trp
1085            1090            1095
Met Gln Lys Leu Asn Gln Val Leu Val Asp Ile Arg Leu Trp Gln
1100            1105            1110

```
Pro Asp  Ala Cys Tyr Lys Pro  Ile Gly Lys Pro
    1115               1120
```